US012410460B2

(12) United States Patent
Jasper et al.

(10) Patent No.: US 12,410,460 B2
(45) Date of Patent: Sep. 9, 2025

(54) BARCODING OF NUCLEIC ACIDS

(71) Applicant: REVVITY HOLDINGS, INC., Boston, MA (US)

(72) Inventors: Melinda Jasper, Collinswood (AU); Steven Myers, Glandore (AU)

(73) Assignee: REVVITY HOLDINGS, INC., Boston, MA (US)

( * ) Notice: Subject to any disclaimer, the term of this patent is extended or adjusted under 35 U.S.C. 154(b) by 871 days.

(21) Appl. No.: 17/285,631

(22) PCT Filed: Oct. 16, 2019

(86) PCT No.: PCT/AU2019/051121
§ 371 (c)(1),
(2) Date: Apr. 15, 2021

(87) PCT Pub. No.: WO2020/077400
PCT Pub. Date: Apr. 23, 2020

(65) Prior Publication Data
US 2021/0381027 A1    Dec. 9, 2021

(30) Foreign Application Priority Data

Oct. 17, 2018  (AU) ............................ 2018903923

(51) Int. Cl.
*C12Q 1/68*      (2018.01)
*C12N 15/10*    (2006.01)
(Continued)

(52) U.S. Cl.
CPC ....... *C12Q 1/6806* (2013.01); *C12N 15/1006* (2013.01); *C12Q 1/6848* (2013.01)

(58) Field of Classification Search
None
See application file for complete search history.

(56) References Cited

U.S. PATENT DOCUMENTS 5,994,058 A    11/1999 Senapathy
6,365,375 B1    4/2002 Dietmaier
(Continued)

FOREIGN PATENT DOCUMENTS

CN    107699957 A    2/2018
EP    2660331 A1    11/2013
(Continued)

OTHER PUBLICATIONS

McClenahan et al, Optimization of virus detection in cells using massively parallel sequencing, Biologicals. Jan. 2014;42(1):34-41. doi: 10.1016/j.biologicals.2013.11.002. Epub Dec. 3, 2013.*
(Continued)

*Primary Examiner* — Aaron A Priest
(74) *Attorney, Agent, or Firm* — White & Case LLP

(57) ABSTRACT

The present disclosure relates to methods, kits and products for barcoding of nucleic acids. In certain embodiments, the present disclosure provides a method of producing nucleic acid for sequencing utilising clonal amplification on a solid substrate, the method comprising: (a) providing a nucleic acid sample for sequencing; (b) amplifying the nucleic acid sample using an amplifying primer comprising a degenerate nucleotide sequence and a 5' fixed nucleotide sequence, to produce amplified nucleic acids; and (c) further amplifying the amplified nucleic acids with (i) a first primer comprising the 5' fixed nucleotide sequence and a first adapter nucleotide sequence, and (ii) a second primer comprising the 5' fixed nucleotide sequence and a second adapter nucleotide sequence, wherein the first adapter nucleotide sequence or the second adapter nucleotide sequence provides a sequence for subsequent priming of DNA synthesis from a nucleotide sequence attached to the solid substrate and the other adapter nucleotide sequence provides a sequence for subsequent priming of DNA synthesis from a template produced from
(Continued)

Step 1a – TSE universal seq forward target-specific sequence
5'-CCAGCCTTGCXXXXXXXXXXXXXXXXXXXXX-3' universal seq reverse target-specific sequence
5'-CCAGCCTTGCYYYYYYYYYYYYYYYYYYYYY-3'

Step 2a – gene-specific amplification universal seq forward target-specific sequence
5'-CCAGCCTTGCXXXXXXXXXXXXXXXXXXXXX-3' universal seq reverse target-specific sequence
5'-CCAGCCTTGCYYYYYYYYYYYYYYYYYYYYY-3' the subsequent priming, and wherein one or more of the first primer, the second primer and the amplifying primer comprise a specific identifier sequence to identify nucleic acids amplified with the first primer, the second primer and/or the amplifying primer; thereby producing nucleic acid for sequencing utilising clonal amplification on the solid substrate.

17 Claims, 30 Drawing Sheets

Specification includes a Sequence Listing.

(51) Int. Cl.
   C12Q 1/6806      (2018.01)
   C12Q 1/6848      (2018.01)

(56) References Cited

U.S. PATENT DOCUMENTS

| | | | |
|---|---|---|---|
| 9,249,459 B2 | 2/2016 | Hamilton et al. | |
| 2010/0184152 A1 | 7/2010 | Sandler et al. | |
| 2011/0033862 A1 | 2/2011 | Rabinowitz et al. | |
| 2014/0017683 A1* | 1/2014 | Yin | C12Q 1/6888 435/6.11 |
| 2020/0248264 A1* | 8/2020 | Rabinowitz | C12Q 1/6855 |

FOREIGN PATENT DOCUMENTS

| | | | | |
|---|---|---|---|---|
| EP | 2770090 B1 * | 4/2018 | | C12N 15/1093 |
| WO | WO-2009105531 A1 | 8/2009 | | |
| WO | WO-2011131192 A1 | 10/2011 | | |
| WO | WO 2016/010856 A1 | 1/2016 | | |
| WO | WO 2017/165925 A1 | 10/2017 | | |

OTHER PUBLICATIONS

Roche, KAPA Adapter Kits Ion Torrent™ Platforms, KR0574—v3. 16, Oct. 2016.*
GenBank Accession No. HO910453, published Oct. 25, 2010 (1 page).
International Search Report PCT/AU2019/051121, dated Dec. 28, 2019 (7 pages).
McClenahan et al., "Optimizaton of virus detection in cells using massively parallel sequencing," Biologicals, vol. 42(1): 34-41 (2014).
China P10136-PI.210702 First Office Action, Jul. 2, 2021 (5 pages).
Chinese Patent Application No. 201780033969.0 (translation), Applicant: PerkinElmer Health Sciences (Australia) Pty Ltd, Text of First Office Action titled Amplification of Target Sequences, POF Ref. FF56185/18 (3 pages).
Cheung, Whole genome amplification using a degenerate oligonucleotide primer allows hundreds of genotypes to be performed on less than one nanogram of genomic DNA, PNAS, vol. 93(25): 14676-14679 (1996).
EPO Communication Pursuant to Article 94(3), Application No. 17 772 883.9-1118, dated Jun. 16, 2021 (9 pages).
India First Examination Report, Application No. 201837040731 dated Mar. 22, 2021 (6 pages).
India Hearing Notice dated Jan. 28, 2022, POK/Application No. 201837040731 (3 pages).
Lorenz, Polymerase Chain Reaction: Basic Protocol Plus Troubleshooting and Optimization Strategies, J. Vis. Exp. vol. 63: e3998 (2012). (2012).
Martino et al., "Novel degenerate PCR method for whole-genome amplification applied to Peru Margin (ODP Leg 201) subsurface samples," Frontiers in Microbiology, vol. 3(17): 1-11 (2012).
Nakayama et al., "Isolation of the 5'-flanking region of genes by thermal asymmetric interlaced polymerase chain reaction," Med Sci monit, vol. 7(3): 345-349 (2001).
Pich, Utility of DNA amplified by degenerate oligonucleotide-primed PCT (DOP-PCR) from the total genome and defined chromosomal regions of field bean, Mol. Gen. Genet. vol. 243: 173-177 (1994).
Telenius et al., "Degenerate Oligonucleotide-Primed PCR: General Amplification of Targe DNA by a Single Degenerate Primer," Genomics, vol. 13: 178-725 (1992).
Supplementary European Search Report EP 19 87 3852, dated Jun. 14, 2022 (3 pages).
Wang et al., "Fusion primer and nested integrated PCR (FPNI-PCR): a new high-efficiency strategy for rapid chromosome walking or flanking sequence cloning," BMC Biotechnology, vol. 11(109) 12 pages (2011).
Ferrarini et al., "A streamlined workflow for single-cells genome-wide copy-number profiling by low-pass sequencing of LM-PCT whole-genome amplification products," PLOS One, vol. 13(3): e0193689: 1-24 (2018).
Kitson et al., "Detecting host-parasitoid interactions in an invasive Lepidopteran using nested tagging DNA-metabarcoding," Internet <https://doi.org/10.1101/035071>, Jan. 2019.
Miya et al., "MIFish, a set of universal PCR primers for metabarcoding environmental DNA from fishes: detection of more than 230 subtropical marine species," The Royal Society Open Science, vol. 2:150088: 1-33 (2015).

* cited by examiner

Figure 4: WGA example with TSE

Lanes 1, 2: 10 μM
Lanes 3, 4: 5 μM
Lanes 5, 6: 2.5 μM
Lane 7: Control WGA sample with no TSE primers
Lane 8: NTC
Lane 9: DNA ladder

M8-DOP - used in WGA PCR
    universal seq  DOP sequence
5'-CCAGCCTTGCNNNNNNATGTGG-3'

M8-TSE-F - added to WGA PCR
universal seq  reverse gene-specific sequence
5'-CCAGCCTTGCXXXXXXXXXXXXXXXXXXXXX-3'
X denotes gene-specific primer sequence; in most cases non-degenerate and between 18-25 bases long.

M8-TSE-R - added to WGA PCR
    universal seq  reverse gene-specific sequence
5'-CCAGCCTTGCYYYYYYYYYYYYYYYYYYYYY-3'
Y denotes gene-specific primer sequence; in most cases non-degenerate and between 18-25 bases long.

M8-A-BCXX - used in adapter/index PCR (and adapter/index PCR of gene-specific)
    A-adapter                                                barcode*    universal seq
5'-CCATCTCATCCCTGCGTGTCTCCGACTCAGGATTCTAACGGACCCAGCCTTGC-3'

M8-P1 - used in adapter/index PCR (and adapter/index PCR of gene-specific)
    P1-adapter                                                  universal seq
5'-CCACTACGCCTCCGCTTTCCTCTCTATGGGCAGTCGGTGATCCAGCCTTGC-3'

*Fig. 6*

M8-DOP - used in WGA PCR
   universal seq  DOP sequence
5'-CCAGCCTTGCNNNNNNATGTGG-3'

M8-A-BCXX - used in adapter/index PCR (and adapter/index PCR of gene-specific)
   A-adapter                                               barcode*    universal seq
5'-CCATCTCATCCCTGCGTGTCTCCGACTCAGGATTCTAACGGACCCAGCCTTGC-3'

M8-P1 - used in adapter/index PCR (and adapter/index PCR of gene-specific)
   P1-adapter                                                         universal seq
5'-CCACTACGCCTCCGCTTTCCTCTCTATGGGCAGTCGGTGATCCAGCCTTGC-3'

Step 1a – TSE universal seq forward target-specific sequence      universal seq reverse target-specific sequence
5'-CCAGCCTTGCXXXXXXXXXXXXXXXXXXXX-3'      5'-CCAGCCTTGCYYYYYYYYYYYYYYYYYYYY-3'

5'-CCAGCCTTGCXXXXXXXXXXNNNNNNNNNNNNATGNNNNNNNNNNYYYYYYYYYYYYYYYYNNNNNNNNNCACANNNNNGCAAGGTTGG-3'
3'-NNNNNNNNNNNNNTACNNNNNNNNNNYYYYYYYYYYYYYYYYNNNNNNNNNGTGTNNNNNCGTTCCAACC-5'
                ← AMPLIFICATION

Step 2a – gene-specific amplification universal seq forward target-specific sequence      universal seq reverse target-specific sequence
5'-CCAGCCTTGCXXXXXXXXXXXXXXXXXXXX-3'      5'-CCAGCCTTGCYYYYYYYYYYYYYYYYYYYY-3'

5'-CCAGCCTTGCXXXXXXXXXXNNNNNNNNNNNNATGNNNNNNNNNNYYYYYYYYYYYYYYYYNNNNNNNNNCACANNNNNGCAAGGTTGG-3'
3'-YYYYYYYYYYYYYYYYYYYYGGTACCGACC-5'
                ← AMPLIFICATION

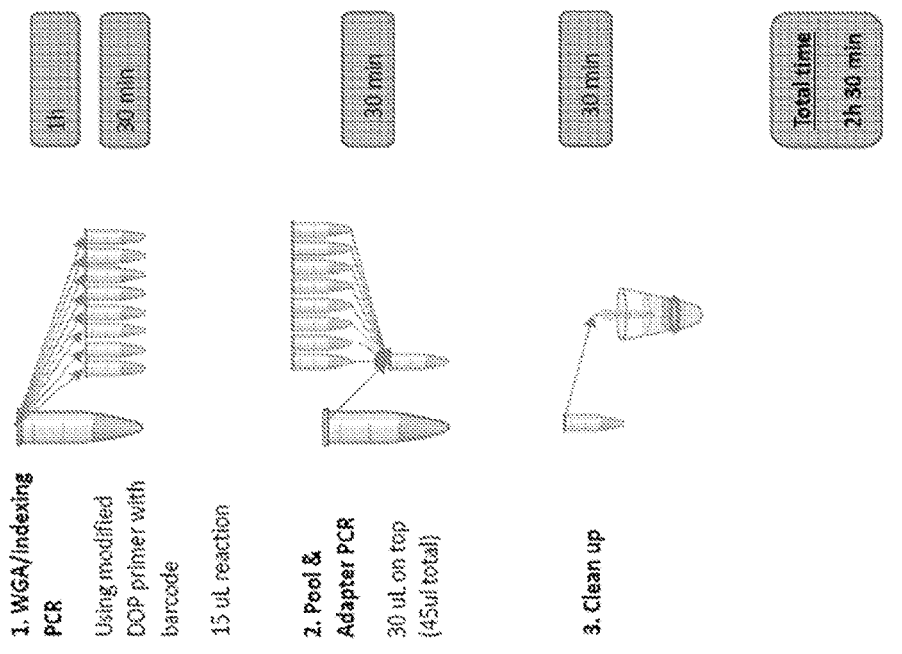
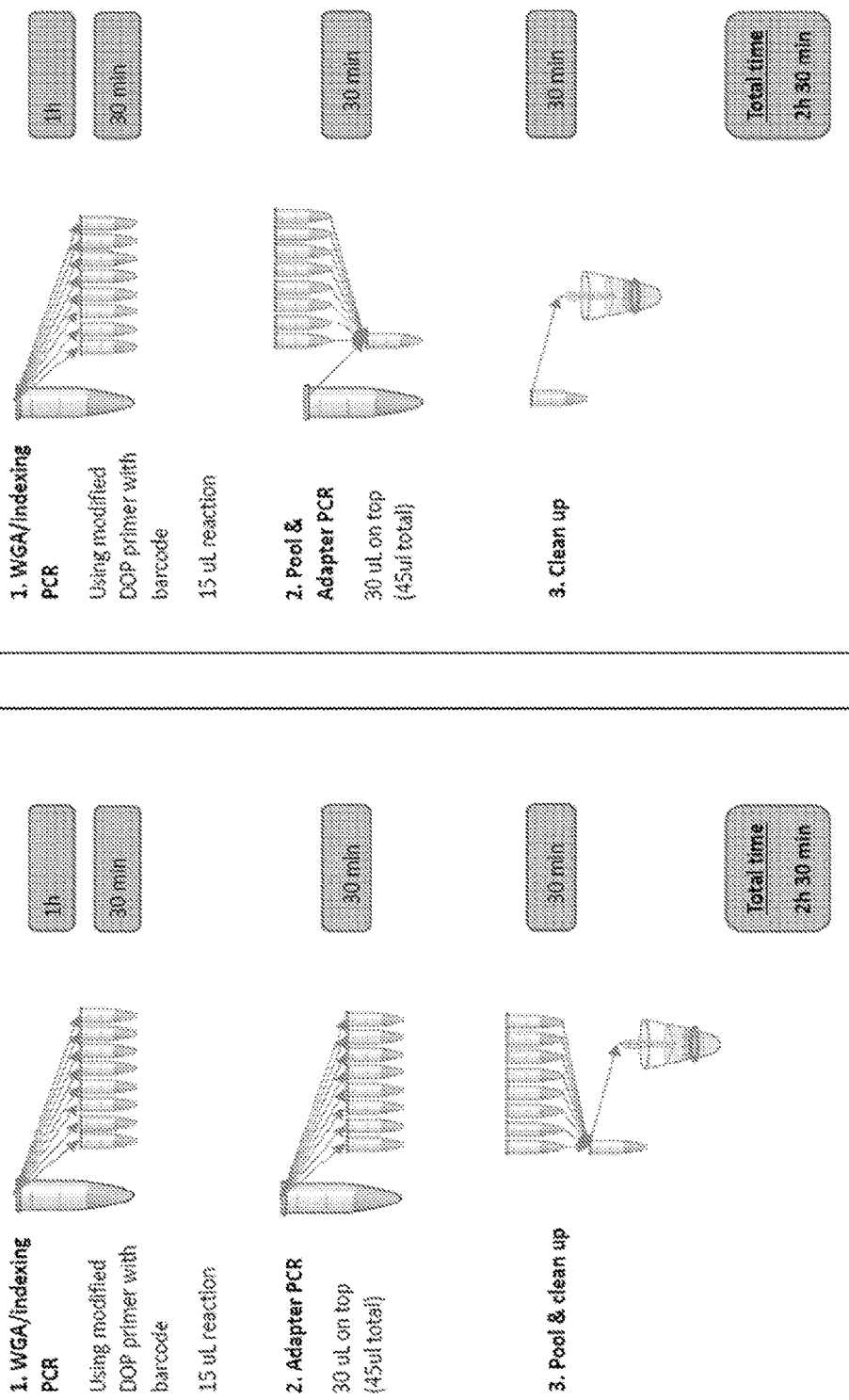
Fig. 14

Fig. 15

M6-6MW-BCXX - used in WGA/indexing PCR

*barcode\**      *universal seq*    *DOP sequence*

5'-TCTAACGGACCCAGCCTTGCNNNNNATGTGG-3'

M6-A-BCXX - used in adapter PCR

Adapter A      *barcode\**      *universal seq*

5'-CCATCTCATCCCTGCGTGTCTCCGACTCAGGATTCTAACGGACCCAGCCTTGC-3'

M6-P1-BCXX - used in adapter PCR

Adapter P1      *barcode\**      *universal seq*

5'-CCGCTTTCCTCTCTATGGGCAGTCGGTGATTCTAACGGACCCAGCCTTGC-3'

*\*Barcode sequence is variable*

Fig. 16

Step 1 – WGA/indexing PCR barcode*    universal seq    DOP sequence
5'-TCTAACGGACCAGCCTTGCNNNNNATGTGG-3'

Step 2 – Adapter PCR

Adapter A      barcode*    universal seq
5'-CCATCTCATCCCTGCGTGTCTCCGACTCAGGATTCTAACGGACCAGCCTTGC-3'

Adapter P1      barcode*    universal seq
5'-CCGCTTTCCTCTCTATGGGCAGTCGGTGATTCTAACGGACCAGCCTTGC-3'

Fig. 19

Step 1 – WGA (modified DOP-PCR)

Part of adapter A    barcode    Matching 3' DOP primer
5'-GTCTCCGACTCAGNNNNNNNGATNNNNNATGTGG-3'

Step 2 – amplification

Truncated Adapter A (including priming site)    Adapter P1    Matching 3' DOP primer
5'-CCATCTCATCCCTGCGTGTCTCCGACTCAG-3'    5'-CCTCTCTATGGGCAGTCGGTGATNNNNNATGTGG-3'

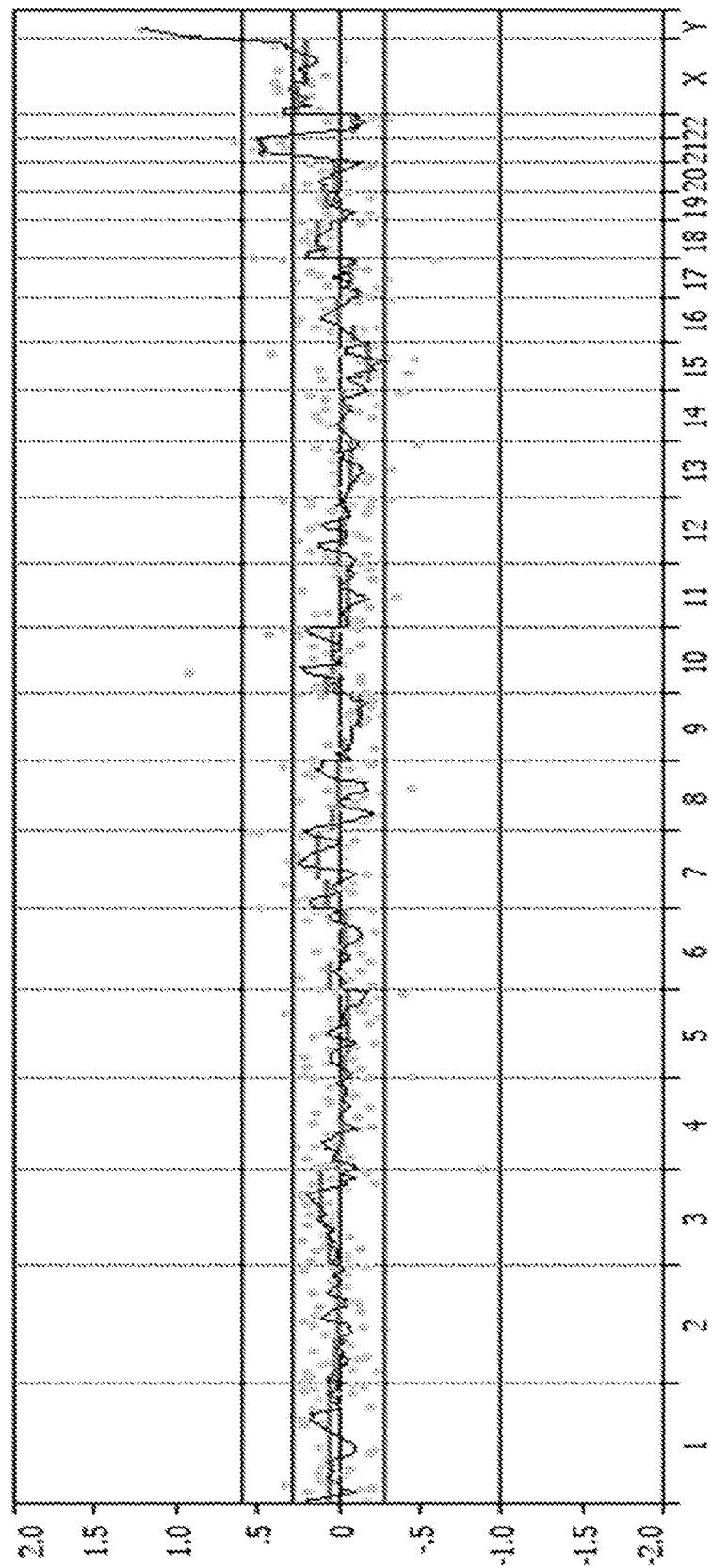

Fig. 22 universal read    universal DOP
5'-GCTCTTCCGATCTACTCGAGNNNNNNATGTGG-3'

P5-adapter                     P5-read                    universal read    universal
5'-AATGATACGGCGACCACCGAGATCTACACTCTTTCCCTACACGACGCTCTTCCGATCTACTCGAG-3'    54°C/77°C P7-adapter                            barcode   P7-read        universal read    universal
5'-CAAGCAGAAGACGGCATACGAGATNNNNNNNNGTGACTGGAGTTCAGACGTGTGCTCTTCCGATCTACTCGAG-3'
54°C/79°C

```
           universal read    barcode    DOP
5'-GCTCTTCCGATCTNNNNNNNNGAGNNNNNNATGTGG-3'

P5-adapter                    P5-read                    universal read
5'-AATGATACGGCGACCACCGAGATCTACACTCTTTCCCTACACGACGCTCTTCCGATCT-3'
       P7-adapter                    P7-read                    universal read
5'-CAAGCAGAAGACGGCATACGAGATGTGACTGGAGTTCAGACGTGTGCTCTTCCGATCT-3'
```

*Fig. 24*

SEQUENCE LISTING

```
<160> NUMBER OF SEQ ID NOS: 52

<210> SEQ ID NO 1
<211> LENGTH: 22
<212> TYPE: DNA
<213> ORGANISM: Artificial Sequence
<220> FEATURE:
<223> OTHER INFORMATION: Amplifying primer
<220> FEATURE:
<221> NAME/KEY: misc_feature
<223> OTHER INFORMATION: Degenerate nucleotide sequence N any nucleotide
<220> FEATURE:
<221> NAME/KEY: misc_feature
<222> LOCATION: (11)..(16)
<223> OTHER INFORMATION: N any nucleotide

<400> SEQUENCE: 1
ccagccttgc nnnnnnatgt gg                                              22

<210> SEQ ID NO 2
<211> LENGTH: 10
```

```
<212> TYPE: DNA
<213> ORGANISM: Artificial Sequence
<220> FEATURE:
<223> OTHER INFORMATION: 5' fixed sequence

<400> SEQUENCE: 2
ccagccttgc                                                                  10

<210> SEQ ID NO 3
<211> LENGTH: 10
<212> TYPE: DNA
<213> ORGANISM: Artificial Sequence
<220> FEATURE:
<223> OTHER INFORMATION: Example of barcode sequence

<400> SEQUENCE: 3
tctaacggac                                                                  10

<210> SEQ ID NO 4
<211> LENGTH: 30
<212> TYPE: DNA
<213> ORGANISM: Artificial Sequence
<220> FEATURE:
<223> OTHER INFORMATION: A-adapter sequence

<400> SEQUENCE: 4
ccatctcatc cctgcgtgtc tccgactcag                                             30

<210> SEQ ID NO 5
<211> LENGTH: 53
<212> TYPE: DNA
<213> ORGANISM: Artificial Sequence
<220> FEATURE:
<223> OTHER INFORMATION: Primer sequence

<400> SEQUENCE: 5
ccatctcatc cctgcgtgtc tccgactcag gattctaacg gacccagcct tgc                   53

<210> SEQ ID NO 6
<211> LENGTH: 50
<212> TYPE: DNA
<213> ORGANISM: Artificial Sequence
<220> FEATURE:
<223> OTHER INFORMATION: Primer sequence

<400> SEQUENCE: 6
cactacgcct ccgctttcct ctctatgggc agtcggtgat ccagccttgc                       50

<210> SEQ ID NO 7
<211> LENGTH: 40
<212> TYPE: DNA
<213> ORGANISM: Artificial Sequence
<220> FEATURE:
<223> OTHER INFORMATION: P1-adapter sequence

<400> SEQUENCE: 7
cactacgcct ccgctttcct ctctatgggc agtcggtgat                                  40

<210> SEQ ID NO 8
<211> LENGTH: 50
<212> TYPE: DNA
<213> ORGANISM: Artificial Sequence
<220> FEATURE:
<223> OTHER INFORMATION: Primer sequence
```

```
<400> SEQUENCE: 8
ccatctcatc cctgcgtgtc tccgactcag tctaacggac ccagccttgc            50

<210> SEQ ID NO 9
<211> LENGTH: 32
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (21)..(26)
<223> OTHER INFORMATION: N any nucleotide

<400> SEQUENCE: 9
tctaacggac ccagccttgc nnnnnnatgt gg                               32

<210> SEQ ID NO 10
<211> LENGTH: 50
<212> TYPE: DNA
<213> ORGANISM: Artificial Sequence
<220> FEATURE:
<223> OTHER INFORMATION: Primer sequence

<400> SEQUENCE: 10
ccgctttcct ctctatgggc agtcggtgat tctaacggac ccagccttgc            50

<210> SEQ ID NO 11
<211> LENGTH: 30
<212> TYPE: DNA
<213> ORGANISM: Artificial Sequence
<220> FEATURE:
<223> OTHER INFORMATION: P1-adapter

<400> SEQUENCE: 11
ccgctttcct ctctatgggc agtcggtgat                                  30

<210> SEQ ID NO 12
<211> LENGTH: 15
<212> TYPE: DNA
<213> ORGANISM: Artificial Sequence
<220> FEATURE:
<223> OTHER INFORMATION: modified DOP-PCR
<220> FEATURE:
<221> NAME/KEY: misc_feature
<222> LOCATION: (4)..(9)
<223> OTHER INFORMATION: N any nucleoide

<400> SEQUENCE: 12
gatnnnnnna tgtgg                                                  15

<210> SEQ ID NO 13
<211> LENGTH: 13
<212> TYPE: DNA
<213> ORGANISM: Artificial Sequence
<220> FEATURE:
<223> OTHER INFORMATION: Part of A adapter

<400> SEQUENCE: 13
gtctccgact cag                                                    13

<210> SEQ ID NO 14
<211> LENGTH: 30
<212> TYPE: DNA
<213> ORGANISM: Artificial Sequence
<220> FEATURE:
```

```
<223> OTHER INFORMATION: Primer sequence

<400> SEQUENCE: 14
ccatctcatc cctgcgtgtc tccgactcag                                          30

<210> SEQ ID NO 15
<211> LENGTH: 35
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (24)..(29)
<223> OTHER INFORMATION: n is a, c, g, or t

<400> SEQUENCE: 15
cctctctatg ggcagtcggt gatnnnnnna tgtgg                                    35

<210> SEQ ID NO 16
<211> LENGTH: 20
<212> TYPE: DNA
<213> ORGANISM: Artificial Sequence
<220> FEATURE:
<223> OTHER INFORMATION: Adapter P1 sequence

<400> SEQUENCE: 16
cctctctatg ggcagtcggt                                                     20

<210> SEQ ID NO 17
<211> LENGTH: 33
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (21)..(27)
<223> OTHER INFORMATION: n is a, c, g, or t

<400> SEQUENCE: 17
gctcttccga tctactcgag nnnnnnnatg tgg                                      33

<210> SEQ ID NO 18
<211> LENGTH: 20
<212> TYPE: DNA
<213> ORGANISM: Artificial Sequence
<220> FEATURE:
<223> OTHER INFORMATION: 5' fixed sequence

<400> SEQUENCE: 18
gctcttccga tctactcgag                                                     20

<210> SEQ ID NO 19
<211> LENGTH: 65
<212> TYPE: DNA
<213> ORGANISM: Artificial Sequence
<220> FEATURE:
<223> OTHER INFORMATION: Primer sequence

<400> SEQUENCE: 19
aatgatacgg cgaccaccga gatctacact ctttccctac acgacgctct tccgatctac         60
tcgag                                                                     65

<210> SEQ ID NO 20
<211> LENGTH: 45
```

```
<212> TYPE: DNA
<213> ORGANISM: Artificial Sequence
<220> FEATURE:
<223> OTHER INFORMATION: P5 adapter sequence

<400> SEQUENCE: 20
aatgatacgg cgaccaccga gatctacact ctttccctac acgac         45

<210> SEQ ID NO 21
<211> LENGTH: 24
<212> TYPE: DNA
<213> ORGANISM: Artificial Sequence
<220> FEATURE:
<223> OTHER INFORMATION: P7 adapter sequence

<400> SEQUENCE: 21
caagcagaag acggcatacg agat                                24

<210> SEQ ID NO 22
<211> LENGTH: 73
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (25)..(32)
<223> OTHER INFORMATION: N selected nucleotide

<400> SEQUENCE: 22
caagcagaag acggcatacg agatnnnnnn nngtgactgg agttcagacg tgtgctcttc    60
cgatctactc gag                                                      73

<210> SEQ ID NO 23
<211> LENGTH: 10
<212> TYPE: DNA
<213> ORGANISM: Artificial Sequence
<220> FEATURE:
<223> OTHER INFORMATION: nucleotide sequence

<400> SEQUENCE: 23
ccgactcgag                                                10

<210> SEQ ID NO 24
<211> LENGTH: 10
<212> TYPE: DNA
<213> ORGANISM: Artificial Sequence
<220> FEATURE:
<223> OTHER INFORMATION: nucleotide sequence

<400> SEQUENCE: 24
gatgctcgag                                                10

<210> SEQ ID NO 25
<211> LENGTH: 10
<212> TYPE: DNA
<213> ORGANISM: Artificial Sequence
<220> FEATURE:
<223> OTHER INFORMATION: nucleotide sequence

<400> SEQUENCE: 25
gatgccttgc                                                10

<210> SEQ ID NO 26
<211> LENGTH: 13
<212> TYPE: DNA
```

```
<213> ORGANISM: Artificial Sequence
<220> FEATURE:
<223> OTHER INFORMATION: nucleotide sequence

<400> SEQUENCE: 26
gctcttccga tct                                                          13

<210> SEQ ID NO 27
<211> LENGTH: 16
<212> TYPE: DNA
<213> ORGANISM: Artificial Sequence
<220> FEATURE:
<223> OTHER INFORMATION: nucleotide sequence

<400> SEQUENCE: 27
gctcttccga tctgag                                                       16

<210> SEQ ID NO 28
<211> LENGTH: 26
<212> TYPE: DNA
<213> ORGANISM: Artificial Sequence
<220> FEATURE:
<223> OTHER INFORMATION: nucleotide sequence

<400> SEQUENCE: 28
agttcagacg tgtgctcttc cgatct                                            26

<210> SEQ ID NO 29
<211> LENGTH: 22
<212> TYPE: DNA
<213> ORGANISM: Artificial Sequence
<220> FEATURE:
<223> OTHER INFORMATION: nucleotide sequence

<400> SEQUENCE: 29
cagacgtgtg ctcttccgat ct                                                22

<210> SEQ ID NO 30
<211> LENGTH: 18
<212> TYPE: DNA
<213> ORGANISM: Artificial Sequence
<220> FEATURE:
<223> OTHER INFORMATION: nuelcotide sequence

<400> SEQUENCE: 30
ccactacgcc tccgcttt                                                     18

<210> SEQ ID NO 31
<211> LENGTH: 19
<212> TYPE: DNA
<213> ORGANISM: Artificial Sequence
<220> FEATURE:
<223> OTHER INFORMATION: nucleotide sequence

<400> SEQUENCE: 31
tccactacgc ctccgcttt                                                    19

<210> SEQ ID NO 32
<211> LENGTH: 20
<212> TYPE: DNA
<213> ORGANISM: Artificial Sequence
<220> FEATURE:
<223> OTHER INFORMATION: nucleotide sequence

<400> SEQUENCE: 32
ttccactacg cctccgcttt                                                   20
```

```
<210> SEQ ID NO 33
<211> LENGTH: 21
<212> TYPE: DNA
<213> ORGANISM: Artificial Sequence
<220> FEATURE:
<223> OTHER INFORMATION: nucleotide sequence

<400> SEQUENCE: 33
tttccactac gcctccgctt t                                              21

<210> SEQ ID NO 34
<211> LENGTH: 22
<212> TYPE: DNA
<213> ORGANISM: Artificial Sequence
<220> FEATURE:
<223> OTHER INFORMATION: nucleotide sequence

<400> SEQUENCE: 34
ctttccacta cgcctccgct tt                                             22

<210> SEQ ID NO 35
<211> LENGTH: 23
<212> TYPE: DNA
<213> ORGANISM: Artificial Sequence
<220> FEATURE:
<223> OTHER INFORMATION: nucleotide sequence

<400> SEQUENCE: 35
gctttccact acgcctccgc ttt                                            23

<210> SEQ ID NO 36
<211> LENGTH: 24
<212> TYPE: DNA
<213> ORGANISM: Artificial Sequence
<220> FEATURE:
<223> OTHER INFORMATION: nucleotide sequence

<400> SEQUENCE: 36
cgctttccac tacgcctccg cttt                                           24

<210> SEQ ID NO 37
<211> LENGTH: 25
<212> TYPE: DNA
<213> ORGANISM: Artificial Sequence
<220> FEATURE:
<223> OTHER INFORMATION: nucleotide sequence

<400> SEQUENCE: 37
ccgctttcca ctacgcctcc gcttt                                          25

<210> SEQ ID NO 38
<211> LENGTH: 10
<212> TYPE: DNA
<213> ORGANISM: Artificial Sequence
<220> FEATURE:
<223> OTHER INFORMATION: nucleotide sequence

<400> SEQUENCE: 38
ctaaggtaac                                                           10

<210> SEQ ID NO 39
<211> LENGTH: 10
<212> TYPE: DNA
<213> ORGANISM: Artificial Sequence
<220> FEATURE:
```

<223> OTHER INFORMATION: artificial sequence

<400> SEQUENCE: 39
taaggagaac                                                              10

<210> SEQ ID NO 40
<211> LENGTH: 10
<212> TYPE: DNA
<213> ORGANISM: Artificial Sequence
<220> FEATURE:
<223> OTHER INFORMATION: nucleotide sequence

<400> SEQUENCE: 40
aagaggattc                                                              10

<210> SEQ ID NO 41
<211> LENGTH: 10
<212> TYPE: DNA
<213> ORGANISM: Artificial Sequence
<220> FEATURE:
<223> OTHER INFORMATION: nucleotide sequence

<400> SEQUENCE: 41
taccaagatc                                                              10

<210> SEQ ID NO 42
<211> LENGTH: 10
<212> TYPE: DNA
<213> ORGANISM: Artificial Sequence
<220> FEATURE:
<223> OTHER INFORMATION: nucleotide sequence

<400> SEQUENCE: 42
cagaaggaac                                                              10

<210> SEQ ID NO 43
<211> LENGTH: 10
<212> TYPE: DNA
<213> ORGANISM: Artificial Sequence
<220> FEATURE:
<223> OTHER INFORMATION: nucleotide sequence

<400> SEQUENCE: 43
ctgcaagttc                                                              10

<210> SEQ ID NO 44
<211> LENGTH: 10
<212> TYPE: DNA
<213> ORGANISM: Artificial Sequence
<220> FEATURE:
<223> OTHER INFORMATION: nucelotide sequence

<400> SEQUENCE: 44
ttcgtgattc                                                              10

<210> SEQ ID NO 45
<211> LENGTH: 10
<212> TYPE: DNA
<213> ORGANISM: Artificial Sequence
<220> FEATURE:
<223> OTHER INFORMATION: nucleotide sequence

<400> SEQUENCE: 45
ttccgataac                                                              10

<210> SEQ ID NO 46
<211> LENGTH: 10
<212> TYPE: DNA
<213> ORGANISM: Artificial Sequence
<220> FEATURE:
<223> OTHER INFORMATION: nucleotide sequence

<400> SEQUENCE: 46
tgagcggaac                                                                 10

<210> SEQ ID NO 47
<211> LENGTH: 23
<212> TYPE: DNA
<213> ORGANISM: Artificial Sequence
<220> FEATURE:
<223> OTHER INFORMATION: nucleotide sequence

<400> SEQUENCE: 47
cctctctatg ggcagtcggt gat                                                  23

<210> SEQ ID NO 48
<211> LENGTH: 40
<212> TYPE: DNA
<213> ORGANISM: Artificial Sequence
<220> FEATURE:
<223> OTHER INFORMATION: Part of primer sequence

<400> SEQUENCE: 48
acactctttc cctacacgac gctcttccga tctactcgag                                40

<210> SEQ ID NO 49
<211> LENGTH: 25
<212> TYPE: DNA
<213> ORGANISM: Artificial Sequence
<220> FEATURE:
<223> OTHER INFORMATION: P5 adapter sequence

<400> SEQUENCE: 49
aatgatacgg cgaccaccga gatct                                                25

<210> SEQ ID NO 50
<211> LENGTH: 58
<212> TYPE: DNA
<213> ORGANISM: Artificial Sequence
<220> FEATURE:
<223> OTHER INFORMATION: primer sequence

<400> SEQUENCE: 50
aatgatacgg cgaccaccga gatctacact ctttccctac acgacgctct tccgatct           58

<210> SEQ ID NO 51
<211> LENGTH: 58
<212> TYPE: DNA
<213> ORGANISM: Artificial Sequence
<220> FEATURE:
<223> OTHER INFORMATION: primer sequence

<400> SEQUENCE: 51
caagcagaag acggcatacg agatgtgact ggagttcaga cgtgtgctct tccgatct           58

<210> SEQ ID NO 52
<211> LENGTH: 13
<212> TYPE: DNA
<213> ORGANISM: Artificial Sequence
<220> FEATURE:
<223> OTHER INFORMATION: primer sequence

```
<400> SEQUENCE: 52
gtctccgact cag                                                13
```

BARCODING OF NUCLEIC ACIDS

CROSS-REFERENCE TO RELATED APPLICATIONS

This application is a national stage filing under 35 U.S.C. § 371 of International Application No. PCT/AU2019/051121, filed on Oct. 16, 2019, which claims the benefit of and priority to Australian Provisional Application No. 2018903923, filed on Oct. 17, 2018. The specifications of each of the foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 7, 2021, is named 1861599-0002-051-301_Seq.txt and is 10,901 bytes in size.

FIELD

The present disclosure relates to methods, kits and products for barcoding of nucleic acids.

BACKGROUND

Advances in DNA sequencing technologies have driven a desire to increase the amount and type of sequence data that can be obtained from single runs on high throughput sequencing platforms. Multiplex sequencing allows large numbers of libraries to be pooled and sequenced simultaneously during a single run, and is particularly advantageous when performing low pass sequencing for copy number detection and targeting specific genomic regions at the same time.

The use of "barcode" sequences has been adopted to assist with multiplex sequencing. Individual barcode sequences are added to each DNA fragment of a sample during next-generation sequencing ("NGS") library preparation so that each read can be identified as belonging to that sample and sorted into a sample bin before the final data analysis. Pooling samples increases the number of samples able to be analysed in a single NGS run, dramatically decreasing the sequencing cost and time.

Whole Genome Amplification ("WGA") protocols have been developed to assist with sequencing methods, particularly under circumstances where the amount of input DNA is limited. For example, WGA methods are used as the first step to provide enough DNA for library preparation to prepare embryo biopsies for NGS, such as for Preimplantation Genetic Testing for Aneuploidy ("PGT-A") WGA may not only be used to amplify whole genomes, but also allows enrichment of target sequences for sequencing.

The incorporation of PCR barcoding during WGA would provide laboratory efficiencies compared to sequential WGA followed by standard NGS library preparation, for example by a reduction of operator hands-on time and total protocol time, and decreased reagent requirements for sample preparation.

Accordingly, there is a need to develop new methodologies that allow amplification and PCR barcoding of samples for sequencing.

SUMMARY

The present disclosure relates to methods, kits and products for barcoding of nucleic acids.

Certain embodiments of the present disclosure provide a method of producing nucleic acid for sequencing utilising clonal amplification on a solid substrate, the method comprising:
 (a) providing a nucleic acid sample for sequencing;
 (b) amplifying the nucleic acid sample using an amplifying primer comprising a degenerate nucleotide sequence and a 5' fixed nucleotide sequence, to produce amplified nucleic acids; and
 (c) further amplifying the amplified nucleic acids with (i) a first primer comprising the 5' fixed nucleotide sequence and a first adapter nucleotide sequence, and (ii) a second primer comprising the 5' fixed nucleotide sequence and a second adapter nucleotide sequence,
 wherein the first adapter nucleotide sequence or the second adapter nucleotide sequence provides a sequence for subsequent priming of DNA synthesis from a nucleotide sequence attached to the solid substrate and the other adapter nucleotide sequence provides a sequence for subsequent priming of DNA synthesis from a template produced from the subsequent priming, and wherein one or more of the first primer, the second primer and the amplifying primer comprise a specific identifier sequence to identify nucleic acids amplified with the first primer, the second primer and/or the amplifying primer;
 thereby producing nucleic acid for sequencing utilising clonal amplification on the solid substrate.

Certain embodiments of the present disclosure provide a kit for producing a nucleic acid for sequencing using a method as described herein.

Certain embodiments of the present disclosure provide nucleic acid for sequencing produced by a method as described herein.

Certain embodiments of the present disclosure provide a solid substrate comprising nucleic acid as described herein.

Certain embodiments of the present disclosure provide a method of sequencing nucleic acid, the method comprising producing nucleic acid for sequencing by a method as described herein and sequencing the nucleic acid.

Certain embodiments of the present disclosure provide a method of sequencing nucleic acid, the method comprising:
 (a) providing a nucleic acid sample for sequencing;
 (b) amplifying the nucleic acid sample using an amplifying primer comprising a degenerate nucleotide sequence and a 5' fixed nucleotide sequence, to produce amplified nucleic acids; and
 (c) further amplifying the amplified nucleic acids with (i) a first primer comprising the 5' fixed nucleotide sequence and a first adapter nucleotide sequence, and (ii) a second primer comprising the 5' fixed nucleotide sequence and a second adapter nucleotide sequence,
 wherein the first adapter nucleotide sequence or the second adapter nucleotide sequence provides a sequence for subsequent priming of DNA synthesis from a nucleotide sequence attached to the solid substrate and the other adapter nucleotide sequence provides a sequence for subsequent priming of DNA synthesis from a template produced from the subsequent priming, and wherein one or more of the first primer, the second primer and the amplifying primer comprise a specific identifier sequence to identify nucleic acids amplified with the first primer, the second primer and/or the amplifying primer, to produce further amplified nucleic acid; and
 (d) sequencing the further amplified nucleic acid utilising clonal amplification on a solid substrate.

Certain embodiments of the present disclosure provide a method of sequencing a target, the method comprising:

(a) providing a nucleic acid sample comprising the target for sequencing;

(b) amplifying the nucleic acid sample using an amplifying primer comprising a degenerate nucleotide sequence and a 5' fixed nucleotide sequence and target specific primers, to produce amplified nucleic acids;

(c) further amplifying the amplified nucleic acids with (i) a first primer comprising the 5' fixed nucleotide sequence and a first adapter nucleotide sequence, (ii) a second primer comprising the 5' fixed nucleotide sequence and a second adapter nucleotide sequence and (iii) target specific primers, wherein the first adapter nucleotide sequence or the second adapter nucleotide sequence provides a sequence for subsequent priming of DNA synthesis from a nucleotide sequence attached to the solid substrate and the other adapter nucleotide sequence provides a sequence for subsequent priming of DNA synthesis from a template produced from the subsequent priming, and wherein one or more of the first primer, the second primer and the amplifying primer comprise a specific identifier sequence to identify nucleic acids amplified with the first primer, the second primer and/or the amplifying primer, to produce further amplified nucleic acid; and (d) sequencing the further amplified nucleic acid utilising clonal target amplification on a solid substrate to sequence the target.

Certain embodiments of the present disclosure provide a method of amplifying a nucleic acid, the method comprising:

(a) providing a nucleic acid sample for sequencing;

(b) amplifying the nucleic acid sample using a primer comprising a degenerate nucleotide sequence and a 5' fixed nucleotide sequence, to produce amplified nucleic acids; and (c) further amplifying the amplified nucleic acids with (i) a first primer comprising the 5' fixed nucleotide sequence and a first adapter nucleotide sequence, and (ii) a second primer comprising the 5' fixed nucleotide sequence and a second adapter nucleotide sequence, wherein the first adapter nucleotide sequence or the second adapter nucleotide sequence provides a sequence for subsequent priming of DNA synthesis from a nucleotide sequence attached to the solid substrate and the other adapter nucleotide sequence provides a sequence for subsequent priming of DNA synthesis from a template produced from the subsequent priming, and wherein one or more of the first primer, the second primer and the amplifying primer comprise a specific identifier sequence to identify nucleic acids amplified with the first primer, the second primer and/or the amplifying primer;

thereby amplifying the nucleic acid.

Certain embodiments of the present disclosure provide a kit for amplifying a nucleic acid using a method as described herein.

Certain embodiments of the present disclosure provide amplified nucleic acid produced by a method as described herein.

Certain embodiments of the present disclosure provide a method of sequencing nucleic acid, the method comprising amplifying nucleic acid by a method as described herein and sequencing the nucleic acid.

Certain embodiments of the present disclosure provide an isolated nucleic acid comprising one of the following nucleotide sequences:

```
                                          (SEQ ID NO: 1)
5'-CCAGCCTTGCNNNNNNNATGTGG-3';

(SEQ ID NO: 8)
5'-CCATCTCATCCCTGCGTGTCTCCGACTCAGTCTAACGGACCCAGCC
TTGC-3';

(SEQ ID NO: 6)
5'-CACTACGCCTCCGCTTTCCTCTCTATGGGCAGTCGGTGATCCAGCC
TTGC-3';

(SEQ ID NO: 9)
5'-TCTAACGGACCCAGCCTTGCNNNNNNNATGTGG-3';
and (SEQ ID NO. 10)
5'-CCGCTTTCCTCTCTATGGGCAGTCGGTGATTCTAACGGACCCAGCC
TTGC-3';
``` or the reverse complement of the aforementioned nucleotide sequences, or a variant of one of the aforementioned nucleotide sequences with at least 90% sequence identity, or the reverse complement with at least 90% sequence identity.

Certain embodiments of the present disclosure provide a method of amplifying nucleic acid comprising using one or more nucleic acids as described herein.

Certain embodiments of the present disclosure provide a kit comprising one or more nucleic acids as described herein.

Other embodiments are described herein.

BRIEF DESCRIPTION OF THE FIGURES

Certain embodiments are illustrated by the following figures. It is to be understood that the following description is for the purpose of describing particular embodiments only and is not intended to be limiting with respect to the description.

FIG. 6 shows primers used in the first work flow of PCR barcoding with target sequence enrichment, according to a first embodiment of the present disclosure.

FIG. 7 shows primers used in each step of a first work flow of PCR barcoding according to a first embodiment of the present disclosure.

FIG. 8 shows primers used for target sequence enrichment in a first work flow of PCR barcoding, and examples of expected PCR products, according to a first embodiment of the present disclosure.

FIG. 14 shows examples of two alternative work flows for an embodiment of the PCR barcoding method, with and without pooling after the first round PCR, according to a second embodiment of the present disclosure.

FIG. 15 shows primers used in a first work flow of PCR barcoding, according to a second embodiment of the present disclosure.

FIG. 16 shows primers used in each step of a first work flow of PCR barcoding, and examples of expected PCR products, according to a second embodiment of the present disclosure.

FIG. 19 shows primers used in each step of a first work flow of PCR barcoding, and examples of PCR products according to a comparative example.

FIG. 22 shows primers used in a first work flow of PCR barcoding according to a further embodiment of the present disclosure.

FIG. 24 shows primers used in a first work flow of PCR barcoding according to a further embodiment of the present disclosure.

DETAILED DESCRIPTION

Figure 1:
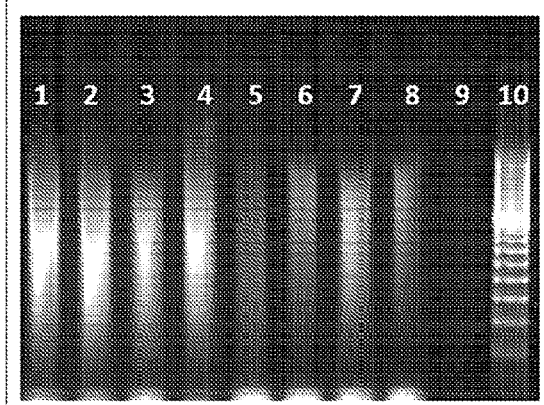
FIG. 1 shows gel electrophoresis of WGA DNA samples prepared using the target sequence enrichment ("TSE") protocol for the amplification of single and multi-cell samples. Lanes 1-4: WGA+TSE using 5-cell samples; Lanes 5-8: WGA+TSE using single-cell samples; Lane 9: NTC; Lane 10: DNA Ladder (100 bp).

The present disclosure relates to methods, kits and products for barcoding of nucleic acids.

The present disclosure is based on the recognition that it is possible to utilise the characteristics of WGA for single tube amplification and barcoding for NGS. The protocol developed has a number of advantages, particularly for preimplantation genetic testing, such as Preimplantation Genetic Testing for Aneuploidy ("PGT-A"), Preimplantation Genetic Testing for Structural Rearrangement ("PGT-SR"), and Preimplantation Genetic Testing for Monogenic diseases ("PGT-M"). For example, in some embodiments, the disclosed methods, products and systems can be used to analyze picogram quantities of DNA (single/multi-cells or low template DNA) from spent embryo culture media, blastomere or trophectoderm embryo biopsy samples, or blastocoelic fluid samples for preimplantation genetic testing.

Certain embodiments of the present disclosure have one or more advantages. For example, some advantages of certain embodiments include a number of laboratory efficiencies compared to sequential NGS library preparation workflows that use WGA followed by DNA fragmentation, end-repair and adapter ligation. The efficiencies include, but are not limited to, one or more of a reduction of operator hands-on time and total protocol time, decreased reagent requirements for sample preparation, a reduction of workflow steps, reduced risk of sample cross contamination, and reduced operator error.

Certain embodiments of the present disclosure provide a method of producing a nucleic acid for sequencing.

In certain embodiments, the present disclosure provides a method of producing nucleic acid for sequencing utilising clonal amplification on a solid substrate, the method comprising:
(a) providing a nucleic acid sample for sequencing;
(b) amplifying the nucleic acid sample using an amplifying primer comprising a degenerate nucleotide sequence and a 5' fixed nucleotide sequence, to produce amplified nucleic acids; and (c) further amplifying the amplified nucleic acids with (i) a first primer comprising the 5' fixed nucleotide sequence and a first adapter nucleotide sequence, and (ii) a second primer comprising the 5' fixed nucleotide sequence and a second adapter nucleotide sequence, wherein the first adapter nucleotide sequence or the second adapter nucleotide sequence provides a sequence for subsequent priming of DNA synthesis from a nucleotide sequence attached to the solid substrate and the other adapter nucleotide sequence provides a sequence for subsequent priming of DNA synthesis from a template produced from the subsequent priming, and wherein one or more of the first primer, the second primer and the amplifying primer comprise a specific identifier sequence to identify nucleic acids amplified with the first primer, the second primer and/or the amplifying primer;

thereby producing nucleic acid for sequencing utilising clonal amplification on the solid substrate.

The term "nucleic acid" as used herein refers to a polynucleotide or an oligonucleotide and includes for example DNA, RNA, DNA/RNA, a variant or DNA and/or RNA (for example a variant of the sugar-phosphate backbone and/or a variant of one or more bases, such as methylation), and may be single stranded, double stranded, non-methylated, methylated, or other forms thereof. In certain embodiments, the nucleic acid is a non-naturally occurring nucleic acid, a naturally occurring nucleic acid, a nucleic acid of genomic origin, a mitochondrial nucleic acid, a nucleic acid of cDNA origin (derived from a mRNA), a nucleic acid derived from a virus, a nucleic acid of synthetic origin, a single stranded DNA, a double stranded DNA, an analogue of DNA and/or RNA, and/or a derivative, fragment and/or combination of any of the aforementioned. Other types of nucleic acids are contemplated.

It will also be appreciated that the term "nucleic acid" includes a single nucleic acid molecule or a plurality of nucleic acid molecules, and for any specific recited sequence described herein the term is to be understood to include the reverse complement of that sequence, or a sequence with at least 90% sequence identity to the recited sequence or the reverse complement.

Nucleic acids for sequencing include DNA, RNA or DNA/RNA hybrids.

Examples of DNA include genomic DNA, cellular DNA, mitochondrial DNA, and viral DNA. DNA may, for example, be isolated, processed or extracted from prokaryotic or eukaryotic cellular DNA, viral DNA, somatic cell DNA, germ cell DNA, gamete DNA, polar body DNA, embryonic cell DNA, fetal DNA, exonic DNA, intronic DNA, non-coding DNA, RNA-coding DNA, non-repetitive DNA, repetitive DNA, transposon DNA, extrachromosomal DNA, organelle DNA, chloroplast DNA, viral DNA, plasmid DNA, nuclear DNA, exosome DNA, extranuclear DNA, cytoplasmic DNA, cDNA, cell-free DNA or synthetic DNA.

In certain embodiments, the nucleic acid for sequencing comprises genomic DNA, mitochondrial DNA, cellular DNA, chloroplast DNA, exosome DNA, locus specific DNA (e.g. a gene or part thereof, one or more exons, one or more introns, a promoter, an enhancer, an untranslated region, a transcribed region), cell-free DNA, cDNA, an extrachromosomal element, bacterial DNA, viral DNA, a vector, a plasmid, non-naturally occurring DNA, RNA, cellular RNA, rRNA, transcribed RNA, mRNA, viral RNA, miRNA, cell-free RNA, or non-naturally occurring RNA. Other types of nucleic acids for sequencing are contemplated.

In certain embodiments the nucleic acid for sequencing comprises DNA or RNA from a single cell, multiple cells, a population of cells, a biopsy, a liquid biopsy, a biological sample, culture media, an embryonic cell, a cancer cell, a cell for genetic testing or cell-free DNA. Other cellular sources of DNA or RNA are contemplated.

A nucleotide sequence used for priming of DNA synthesis refers to a nucleotide sequence used for priming of DNA synthesis of a particular template, or the complement of the nucleotide sequence used for priming of DNA synthesis of a particular template.

Methods for sequencing utilising clonal amplification on a solid substrate are known in the art. These are methods that utilise amplification of a DNA sequence attached to a solid substrate in order to increase the number of DNA sequences that are sequenceable for any particular DNA, leading to an increase in the sequencing signal. Solid substrates are known in the art, such as beads and flow cells, although other types of solid substrates are contemplated.

In certain embodiments, the sequencing utilising clonal amplification comprises methods such as those offered commercially by Illumina (Sequencing-By-Synthesis technology, TruSeq Synthetic Long-Read technology) or ThermoFisher (Ion Torrent technology, Ion Proton technology). Other sequencing methods are contemplated.

For example, Illumina NGS includes the following steps:

(i) Library Preparation—A sequencing library is prepared by random or targeted fragmentation of a DNA or a cDNA sample, followed by 5' and 3' adapter ligation. Adapter-ligated fragments are sometimes then PCR amplified.

(ii) Cluster Generation—For cluster generation, the library is loaded into a flow cell where fragments are captured on a lawn of surface-bound oligonucleotides complementary to the library adapters. Each fragment is then amplified into distinct, clonal clusters through bridge amplification. When cluster generation is complete, the templates are ready for sequencing.

(iii) Sequencing—The technology uses a proprietary reversible terminator-based method that detects single bases as they are incorporated into DNA template strands. As all four reversible terminator-bound dNTPs are present during each sequencing cycle, natural competition minimizes incorporation bias and reduces raw error rates compared to other technologies. The result is highly accurate base-by-base sequencing.

(iv) Data Analysis—During data analysis and alignment, the newly identified sequence reads are aligned to a reference genome. Following alignment, many variations of analysis are possible, such as single nucleotide polymorphism (SNP), single nucleotide variant (SNV), copy number variant (CNV) or insertion-deletion (indel) identification, read counting for DNA methods, read counting for RNA methods, phylogenetic or metagenomic analysis.

Examples of nucleic acid samples include nucleic acids from a single cell, multiple cells, a population of cells, a biopsy, a liquid biopsy, a biological sample, culture media, an embryonic cell, a cancer cell, a cell for genetic testing, or cell-free DNA.

In certain embodiments, the nucleic acid sample for sequencing is nucleic acid that has been processed. For example, nucleic acid from a cell(s) of interest may be obtained by lysis to produce nucleic acid for sequencing.

The term "amplifying", or variants such as "amplification" and "amplified", refers to the process of copying a nucleic acid to produce further copies of all or part of the nucleic acid. For example, amplification of a nucleic acid may be achieved enzymatically using a polymerase chain reaction (PCR), an isothermal method such as multiple displacement amplification using a suitable polymerase or rolling circle amplification. Other types of methods of amplification are contemplated. Methods for performing amplification are described herein.

Methods for amplifying nucleic acids are known in the art.

In certain embodiments, the amplifying comprises a polymerase chain reaction. Methods for using a polymerase chain reaction are as described herein. Methods for performing amplification are described, for example, in Fakruddin et al. (2013) *J Pharm Bioall Sci* 5(4): 245-252.

In certain embodiments, the amplifying comprises an isothermal amplification reaction. Methods for performing isothermal amplification are known in the art, such as loop-mediated isothermal amplification (LAMP), strand displacement amplification (SDA), multiple displacement amplification (MDA), linear amplification e.g. via transport insertion (LIANTI), helicase-dependent amplification (HDA), and nicking enzyme amplification reaction (NEAR). In certain embodiments, the amplifying comprises a reaction using Multiple Displacement Amplification. Methods for performing Multiple Displacement Amplification WGA are known in the art, for example as described in Dean et al. (2002) *Proc Natl. Acad. Sci USA* 99: 5261. In certain embodiments, the amplifying comprises a reaction using rolling circle amplification. Other types of amplification are contemplated. Methods for amplifying are as described, for example, in Walker et al. (1992) *Nucleic Acids Res.* 20:1691-1696, Walker et al. (1993) *PCR Methods Appl.* 3:1-6, Notomi et al. (2000) *Nucleic Acids Res.* 28:e63, Tomita N et al. (2008) *Nat. Protoc.* 3:877-882, Lizardi et al. (1998) *Nat. Genet.* 19:225-232, Blanco et al. (1989) *J. Biol. Chem.* 264:8935-8940, and Dean et al. (2001) *Genome Res.* 11:1095-1099, Chen et al. (2017) *Science* 356:189-194, Lage et al. (2003) *Genome Res.* 13:294-307, and Fakruddin et al. (2013) *J Pharm Bioall Sci* 5(4): 245-252.

In certain embodiments, the amplifying comprises whole genome amplification.

Methods for producing primers as described herein are known in the art, such as chemical synthesis. Methods for producing degenerate primers, or primers including a degenerate nucleotide sequence, are known in the art.

The term "degenerate oligonucleotide sequence" refers to either a mix of oligonucleotide sequences in which some positions contain a number of possible bases, giving a population of nucleotides with similar sequences that cover all possible nucleotide combinations, and/or a mix of one or more bases with the ability to bind to more than one base, for example 2-Amino Purine, 5-methyl isodeoxycytosine (Me isodC), 5-nitroindole, inosine deoxy, inosine ribo, or iso deoxyguanosine dG.

In certain embodiments, the degenerate nucleotide sequence of the amplifying primer is a fully degenerate nucleotide sequence.

In certain embodiments, the amplifying primer comprises a degenerate nucleotide sequence of 3 to 16 nucleotides. Other sizes are contemplated.

In certain embodiments, the degenerate nucleotide sequence consists of 6 nucleotides.

In certain embodiments, the amplifying primer comprises a fixed nucleotide sequence 3' to the degenerate nucleotide sequence. Other variations in the relative positioning of the fixed nucleotide sequences to the degenerate oligonucleotide sequence are contemplated.

In certain embodiments, the fixed nucleotide sequence 3' to the degenerate nucleotide sequence comprises 3 to 10 nucleotides.

In certain embodiments, the fixed nucleotide sequence 3' to the degenerate nucleotide sequence consists of a nucleotide sequence of 6 nucleotides.

In certain embodiments, the fixed nucleotide sequence 3' to the degenerate nucleotide sequence consists of the nucleotide sequence 5'-ATGTGG-3', 5'-ATCTCA-3' or 5'-TGAGAT-3.

In certain embodiments, the 5' fixed nucleotide sequence comprises a short motif that occurs at high frequency within a genome (e.g. a repetitive element in the human genome).

In certain embodiments, the 5' fixed nucleotide sequence comprises a nucleotide sequence of 6 to 40 nucleotides. Other sizes are contemplated.

In certain embodiments, the 5' fixed nucleotide sequence consists of a nucleotide sequence of 10 nucleotides.

In certain embodiments, the 5' fixed nucleotide sequence consists of one of the following nucleotide sequences

```
                                           (SEQ ID NO: 2)
5'-CCAGCCTTGC-3';

(SEQ ID NO: 23)
5'-CCGACTCGAG-3';

(SEQ ID NO: 24)
5'-GATGCTCGAG-3';

(SEQ ID NO: 25)
5'-GATGCCTTGC-3';

(SEQ ID NO: 26)
5'-GCTCTTCCGATCT-3';

(SEQ ID NO: 18)
5'-GCTCTTCCGATCTACTCGAG-3';

(SEQ ID NO: 27)
5'-GCTCTTCCGATCTGAG-3';

(SEQ ID NO: 28)
5'-AGTTCAGACGTGTGCTCTTCCGATCT-3';
or (SEQ ID NO: 29)
5'-CAGACGTGTGCTCTTCCGATCT-3'.

(SEQ ID NO. 52)
5'-GTCTCCGACTCAG-3'
```

In certain embodiments, the amplifying of the nucleic acid sample comprises an amount of DNA to be amplified of less than 0.5 pg, less than 1 pg, less than 2.5 pg, less than 5 pg, less than 10 pg, less than 25 pg, less than 50 pg, less than 100 pg, less than 250 pg, less than 500 pg, less than 1 ng, less than 2.5 ng, less than 5 ng or less than 10 ng. Other amounts are contemplated.

In certain embodiments, the amplifying of the nucleic acid sample comprises an amount of DNA to be amplified of at least 0.5 pg, at least 1 pg, at least 2.5 pg, at least 5 pg, at least 10 pg, at least 25 pg, at least 50 pg, at least 100 pg, at least 250 pg, at least 500 pg, at least 1 ng, at least 2.5 ng, at least 5 ng or at least 10 ng. Other amounts are contemplated.

In certain embodiments, the amplifying of the nucleic acid sample comprises an amount of DNA to be amplified of 0.5 pg to 10 ng, 1 pg to 10 ng, 2.5 pg to 10 ng, 5 pg to 10 ng, 10 pg to 10 ng, 25 pg to 10 ng, 50 pg to 10 ng, 100 pg to 10 ng, 250 pg to 10 ng, 500 pg to 10 ng, 1 ng to 10 ng, 2.5 ng to 10 ng, 5 ng to 10 ng, 0.5 pg to 5 ng, 1 pg to 5 ng, 2.5 pg to 5 ng, 5 pg to 5 ng, 10 pg to 5 ng, 25 pg to 5 ng, 50 pg to 5 ng, 100 pg to 5 ng, 250 pg to 5 ng, 500 pg to 5 ng, 1 ng to 5 ng, 2.5 ng to 5 ng, 0.5 pg to2.5 ng, 1 pg to 2.5 ng, 2.5 pg to 2.5 ng, 5 pg to 2.5 ng, 10 pg to 2.5 ng, 25 pg to 2.5 ng, 50 pg to 2.5 ng, 100 pg to 2.5 ng, 250 pg to 2.5 ng, 500 pg to 2.5 ng, 1 ng to 2.5 ng, 0.5 pg to 1 ng, 1 pg to 1 ng, 2.5 pg to 1 ng, 5 pg to 1 ng, 10 pg to 1 ng, 25 pg to 1 ng, 50 pg to 1 ng, 100 pg to 1 ng, 250 pg to 1 ng, 500 pg to 1 ng, 0.5 pg to 500 pg, 1 pg to 500 pg, 2.5 pg to 500 pg, 5 pg to 500 pg, 10 pg to 500 pg, 25 pg to 500 pg, 50 pg to 500 pg, 100 pg to 500 pg, 250 pg to 500 pg, 0.5 pg to 250 pg, 1 pg to250 pg, 2.5 pg to 250 pg, 5 pg to 250 pg, 10 pg to250 pg, 25 pg to 250 pg, 50 pg to 250 pg, 100 pg to 250 pg, 0.5 pg to 100 pg, 1 pg to 100 pg, 2.5 pg to 100 pg, 5 pg to 100 pg, 10 pg to 100 pg, 25 pg to 100 pg, 50 pg to 100 pg, 0.5 pg to 50 pg, 1 pg to 50 pg, 2.5 pg to 50 pg, 5 pg to 50 pg, 10 pg to 50 pg, 25 pg to 50 pg, 0.5 pg to 25 pg, 1 pg to 25 pg, 2.5 pg to 25 pg, 5 pg to 25 pg, 10 pg to 25 pg, 0.5 pg to 10 pg, 1 pg to 10 pg, 2.5 pg to 10 pg, 5 pg to 10 pg, 0.5 pg to 5 ng, 1 pg to 5 ng, 2.5 pg toy pg, 0.5 pg to 2.5 pg, 1 pg to 2.5 pg, or 0.5 p g to 1 pg. Other amounts are contemplated.

In certain embodiments, the nucleic acid sample comprises DNA from 1 to 50 cells. In certain embodiments, the genomic DNA comprises DNA from a single cell, 1 to 10 cells, 1 to 20 cells, 1 to 50 cells, more than 10 cells, less than 10 cells, more than 50 cells, less than 50 cells, more than 100 cells, or less than 100 cells. DNA from other cell numbers is contemplated.

In certain embodiments, the nucleic acid sample comprises RNA from 1 to 50 cells. In certain embodiments, the genomic RNA comprises RNA from a single cell, 1 to 10 cells, 1 to 20 cells, 1 to 50 cells, more than 10 cells, less than 10 cells, more than 50 cells, less than 50 cells, more than 100 cells, or less than 100 cells. RNA from other cell numbers is contemplated.

Examples of types of cells include one or more embryonic cells, an oocyte or a polar body thereof, sperm, one or more germ cells, one or more somatic cells, one or more human cells, one or more animal cells, one or more plant cells, one or more cells from a microorganism, one or more cells for screening for a disease, condition or state, one or more cancerous or pre-cancerous cells, one or more virions, one or more exosomes, cells from a biopsy, one or more fetal cells, cells from a tissue sample, cells in/from a bodily fluid, cells in/from a blood sample, cells in/from amniotic fluid, cells in/from culture media, cells in/from urine, cells in/from plasma, cells in/from serum, cells in/from a cheek scraping, cells from a hair follicle, cells in/from saliva, cells in/from sweat, cells in/from nipple aspirate, cells in/from a formalin fixed sample, cells in/from a paraffin embedded sample, and cells in/from a swab. Other types of cells, and sources of cells, are contemplated. Methods for obtaining cells are known in the art.

In certain embodiments, the first adapter nucleotide sequence comprises the nucleotide sequence 5'-CCGCTTTCCTCTCTATGGGCAGTCGGTGAT-3' (SEQ ID NO: 11).

In certain embodiments, the first adapter nucleotide sequence comprises the nucleotide sequence 5'-CCTCTCTATGGGCAGTCGGTGAT-3' (SEQ ID NO: 47).

In certain embodiments, the second adapter nucleotide sequence comprises the nucleotide sequence 5'-CCATCTCATCCCTGCGTGTCTCCGACTCAG-3' (SEQ ID NO: 4).

In certain embodiments, the first adapter nucleotide sequence further comprises at the 5'-end any part of the 3' end of the nucleotide sequence 5'-CCACTACGCCTCCGCTTT-3' (SEQ ID NO: 30). For example, at the 5' end the first adapter nucleotide sequence may be 5'-TCCACTACGCCTCCGCTTT 3 (SEQ ID NO: 31), 5'-TTCCACTACGCCTCCGCTTT 3' (SEQ ID NO: 32), 5'-TTTCCACTACGCCTCCGCTTT 3' (SEQ ID NO: 33), 5'-CTTTCCACTACGCCTCCGCTTT 3' (SEQ ID NO: 34), 5'-GCTTTCCACTACGCCTCCGCTTT 3' (SEQ ID NO: 35), 5'-CGCTTTCCACTACGCCTCCGCTTT 3' (SEQ ID NO: 36), or 5'-CCGCTTTCCACTACGCCTCCGCTTT 3' (SEQ ID NO: 37), and so forth.

In certain embodiments, the first primer comprises a first adapter nucleotide sequence for subsequent priming of DNA synthesis from the nucleotide sequence attached to the solid substrate and the second primer comprises a second adapter sequence for subsequent priming of DNA synthesis from a template formed from the subsequent priming.

In certain embodiments, the first primer comprises a first adapter nucleotide sequence identical to the nucleotide sequence attached to the solid substrate.

In certain embodiments, the first primer comprises a first adapter nucleotide sequence complementary to the nucleotide sequence attached to the solid substrate In certain embodiments, the first primer and the second primer comprise a nucleotide sequence which is identical or complementary to a nucleotide sequence attached to the solid substrate.

The term "specific identifier sequence" refers to a barcode sequence that permits sorting of nucleic acids sequences for data analysis.

In certain embodiments, the first primer, the second primer and the amplifying primer comprise multiple specific identifier sequences.

In certain embodiments, the first primer, the second primer and the amplifying primer comprise a specific identifier sequence.

In certain embodiments, the specific identifier sequence comprises a nucleotide sequence of 6 to 12 nucleotides.

In certain embodiments, the specific identifier sequence consists of a nucleotide sequence of 10 nucleotides.

In certain embodiments, the specific identifier sequence comprises the nucleotide sequence 5'-TCTAACGGAC-3' (SEQ ID NO: 3).

Examples of other specific identifier sequences are sequences comprising the following nucleotide sequences 5'-CTAAGGTAAC-3' (SEQ ID NO: 38); 5'-TAAGGAGAAC-3' (SEQ ID NO: 39); 5'-AAGAGGATTC-3' (SEQ ID NO: 40); 5'-TACCAAGATC-3' (SEQ ID NO: 41); 5'-CAGAAGGAAC-3' (SEQ ID NO: 42); 5'-CTGCAAGTTC-3' (SEQ ID NO: 43); 5'-TTCGTGATTC-3' (SEQ ID NO: 44); 5'-TTCCGATAAC-3' (SEQ ID NO: 45); and 5'-TGAGCGGAAC-3' (SEQ ID NO: 46).

In certain embodiments, the specific identifier sequence consists of a nucleotide sequence of 8 nucleotides.

In certain embodiments, the specific identifier sequence comprises the nucleotide sequence 5'-TCTCTGTG-3. In certain embodiments, the specific identifier sequence comprises the nucleotide sequence 5'-TGTACGTG-3. In certain embodiments, the specific identifier sequence comprises the nucleotide sequence 5'-ATCGTCTG-3. In certain embodiments, the specific identifier sequence comprises the nucleotide sequence 5'-TAGCTCTG-3. In certain embodiments, the specific identifier sequence comprises the nucleotide sequence 5'-AGTATCTG-3. In certain embodiments, the specific identifier sequence comprises the nucleotide sequence 5'-TCGAGCTG-3. In certain embodiments, the specific identifier sequence comprises the nucleotide sequence 5'-TCATACTG-3. In certain embodiments, the specific identifier sequence comprises the nucleotide sequence 5'-TACGACTG-3. In certain embodiments, the specific identifier sequence comprises the nucleotide sequence 5'-ACTCACTG-3. In certain embodiments, the specific identifier sequence comprises the nucleotide sequence 5'-AGAGTATG-3.

In certain embodiments, the amplifying primer comprises a specific identifier sequence, the first primer comprises a first adapter sequence for subsequent priming of DNA synthesis, and the second primer comprises a nucleotide sequence identical or complementary to a nucleotide sequence attached to the solid substrate and a specific identifier sequence.

In certain embodiments, the first primer comprises a first adapter sequence for subsequent priming of DNA synthesis and a specific identifier sequence, and the second primer comprises a nucleotide sequence identical or complementary to a nucleotide sequence attached to the solid substrate.

In certain embodiments, the first primer comprises a first adapter sequence for subsequent priming of DNA synthesis and a nucleotide sequence identical or complementary to a nucleotide sequence attached to the solid substrate, and the second primer comprises a nucleotide sequence identical or complementary to another nucleotide sequence attached to the solid substrate and a specific identifier sequence.

In certain embodiments, the first primer comprises a first adapter sequence for subsequent priming of DNA synthesis, a nucleotide sequence identical or complementary to a nucleotide sequence attached to the solid substrate and a specific identifier sequence, and the second primer comprises a nucleotide sequence identical or complementary to another nucleotide sequence attached to the solid substrate and the specific identifier sequence.

In certain embodiments, the method further comprises amplifying nucleic acids with one or more target specific primers. Methods for designing target specific primers are known in the art.

In certain embodiments, the method further comprises amplifying with one or more target-specific primers in step (b) and/or further amplifying with one or more target-specific primers in step (c).

In certain embodiments, the method comprises sequencing RNA and RNA is converted to DNA by polymerisation with a reverse transcriptase to produce a nucleic acid sample for sequencing. Methods for converting RNA to DNA with a reverse transcriptase are known in the art.

Certain embodiments of the present disclosure provide a kit for performing a method as described herein.

Certain embodiments of the present disclosure provide a kit for producing a nucleic acid for sequencing using a method as described herein. The kit may contain reagents and/or instructions as described herein.

Certain embodiments of the present disclosure provide nucleic acid for sequencing produced by a method as described herein.

Certain embodiments of the present disclosure provide a solid substrate comprising a nucleic acid produced as described herein.

Methods for attaching nucleic acids to solid substrates for sequencing are known in the art.

In certain embodiments, the solid substrate is a flow cell. In certain embodiments, the solid substrate is a chip.

In certain embodiments, the solid substrate is a bead or Ion Sphere Particle (ISP).

Certain embodiments of the present disclosure provide a method of sequencing nucleic acid, the method comprising producing nucleic acid for sequencing a method as described herein and sequencing the nucleic acid.

Methods for sequencing are known in the art and are as described herein.

In certain embodiments, the nucleic acid for sequencing comprises a specific target.

In certain embodiments, the present disclosure provides a method of sequencing nucleic acid, the method comprising:
(a) providing a nucleic acid sample for sequencing;
(b) amplifying the nucleic acid sample using an amplifying primer comprising a degenerate nucleotide sequence and a 5' fixed nucleotide sequence, to produce amplified nucleic acids; and
(c) further amplifying the amplified nucleic acids with (i) a first primer comprising the 5' fixed nucleotide sequence and a first adapter nucleotide sequence, and (ii) a second primer comprising the 5' fixed nucleotide sequence and a second adapter nucleotide sequence,
wherein the first adapter nucleotide sequence or the second adapter nucleotide sequence provides a sequence for subsequent priming of DNA synthesis from a nucleotide sequence attached to the solid substrate and the other adapter nucleotide sequence provides a sequence for subsequent priming of DNA synthesis from a template produced from the subsequent priming, and wherein one or more of the first primer, the second primer and the amplifying primer comprise a specific identifier sequence to identify nucleic acids amplified with the first primer, the second primer and/or the amplifying primer, to produce further amplified nucleic acid; and
(d) sequencing the further amplified nucleic acid utilising clonal amplification on a solid substrate.

In certain embodiments, the present disclosure provides a method of sequencing a target, the method comprising:
(a) providing a nucleic acid sample comprising the target for sequencing;
(b) amplifying the nucleic acid sample using an amplifying primer comprising a degenerate nucleotide sequence and a 5' fixed nucleotide sequence, and target specific primers, to produce amplified nucleic acids;
(c) further amplifying the amplified nucleic acids with (i) a first primer comprising the 5' fixed nucleotide sequence and a first adapter nucleotide sequence, (ii) a second primer comprising the 5' fixed nucleotide sequence and a second adapter nucleotide sequence and (iii) target specific primers,
wherein the first adapter nucleotide sequence or the second adapter nucleotide sequence provides a sequence for subsequent priming of DNA synthesis a nucleotide sequence attached to the solid substrate and the other adapter nucleotide sequence provides a sequence for subsequent priming of DNA synthesis from a template produced from the subsequent priming, and wherein one or more of the first primer, the second primer and the amplifying primer comprise a specific identifier sequence to identify nucleic acids amplified with the first primer, the second primer and/or the amplifying primer, to produce further amplified nucleic acid; and
(d) sequencing the further amplified nucleic acid utilising clonal amplification on a solid substrate to sequence the target.

Certain embodiments of the present disclosure provide a kit for sequencing using a method as described herein.

Certain embodiments of the present disclosure provide a method of amplifying a nucleic acid.

In certain embodiments, the present disclosure provides a method of amplifying a nucleic acid, the method comprising:
- (a) providing a nucleic acid sample;
- (b) amplifying the nucleic acid sample using a primer comprising a degenerate nucleotide sequence and a 5' fixed nucleotide sequence, to produce amplified nucleic acids; and
- (c) further amplifying the amplified nucleic acids with (i) a first primer comprising the 5' fixed nucleotide sequence and a first adapter nucleotide sequence, and (ii) a second primer comprising the 5' fixed nucleotide sequence and a second adapter nucleotide sequence, wherein the first adapter nucleotide sequence or the second adapter nucleotide sequence provides a sequence for subsequent priming of DNA synthesis from a nucleotide sequence attached to the solid substrate and the other adapter nucleotide sequence provides a sequence for subsequent priming of DNA synthesis from a template produced from the subsequent priming, and wherein one or more of the first primer, the second primer and the amplifying primer comprise a specific identifier sequence to identify nucleic acids amplified with the first primer, the second primer and/or the amplifying primer;

thereby amplifying the nucleic acid.

Methods for assessing amplification of nucleic acids are known in the art.

Certain embodiments of the present disclosure provide a kit for amplifying a nucleic acid using a method as described herein.

The kit may comprise one or more reagents and/or instructions as described herein.

Certain embodiments of the present disclosure provide an amplified nucleic acid produced by a method as described herein.

Certain embodiments of the present disclosure provide a method of sequencing nucleic acid, the method comprising amplifying nucleic acid by a method as described herein and sequencing the nucleic acid.

Certain embodiments of the present disclosure provide a method of producing a nucleic acid for sequencing utilising methods that do not require clonal amplification.

In certain embodiments, the present disclosure provides a method of producing nucleic acid for sequencing, the method comprising:
- (a) providing a nucleic acid sample for sequencing;
- (b) amplifying the nucleic acid sample using an amplifying primer comprising a degenerate nucleotide sequence and a 5' fixed nucleotide sequence, to produce amplified nucleic acids; and
- (c) further amplifying the amplified nucleic acids with (i) a first primer comprising the 5' fixed nucleotide sequence and a first adapter nucleotide sequence, and (ii) a second primer comprising the 5' fixed nucleotide sequence and a second adapter nucleotide sequence, wherein the first adapter nucleotide sequence and/or the second adapter nucleotide sequence provides a sequence for subsequent priming of DNA synthesis, and wherein one or more of the first primer, the second primer and the amplifying primer comprise a specific identifier sequence to identify nucleic acids amplified with the first primer, the second primer and/or the amplifying primer;

thereby producing nucleic acid for sequencing.

Methods and primers for use in this embodiment are as described herein.

In certain embodiments, the sequencing method comprises methods such as those offered commercially by PacBio (SMRT sequencing technology) or Oxford Nanopore Technologies (Nanopore sequencing technology).

In certain embodiments, the sequencing method comprises a method utilising clonal amplification on the solid substrate. Methods for sequencing utilising clonal amplification on a solid substrate are as described herein, and include for example methods such as those offered commercially by Illumina (Sequencing-By-Synthesis technology, TruSeq Synthetic Long-Read technology) or ThermoFisher (Ion Torrent technology, Ion Proton technology).

In certain embodiments, the method is used to sequence a specific target.

In certain embodiments, the method further comprises amplifying nucleic acids with one or more target specific primers. Methods for designing target specific primers are known in the art.

In certain embodiments, the method further comprises amplifying with one or more target-specific primers in step (b) and/or further amplifying with one or more target-specific primers in step (a) described above.

In certain embodiments, the present disclosure provides a method of sequencing nucleic acid, the method comprising:
- (a) providing a nucleic acid sample for sequencing;
- (b) amplifying the nucleic acid sample using an amplifying primer comprising a degenerate nucleotide sequence and a 5' fixed nucleotide sequence, to produce amplified nucleic acids; and
- (c) further amplifying the amplified nucleic acids with (i) a first primer comprising the 5' fixed nucleotide sequence and a first adapter nucleotide sequence, and (ii) a second primer comprising the 5' fixed nucleotide sequence and a second adapter nucleotide sequence, wherein the first adapter nucleotide sequence and/or the second adapter nucleotide sequence provides a sequence for subsequent priming of DNA synthesis, and wherein one or more of the first primer, the second primer and the amplifying primer comprise a specific identifier sequence to identify nucleic acids amplified with the first primer, the second primer and/or the amplifying primer, to produce further amplified nucleic acid; and
- (d) sequencing the further amplified nucleic acid.

Certain embodiments of the present disclosure provide isolated nucleic acids.

The term "isolated" refers to a species, such as a nucleic acid, which has been separated (partially or completely) from its natural or original environment, and includes nucleic acids in a complex mix of other molecules, nucleic acids in a mix of substantially purified nucleic acids, a substantially purified nucleic acid, or a synthesized nucleic acid.

In certain embodiments, the isolated nucleic acid comprises one of the following nucleotide sequences:

```
                                          (SEQ ID NO: 1)
5'-CCAGCCTTGCNNNNNNNATGTGG-3';

(SEQ ID NO: 8)
5'-CCATCTCATCCCTGCGTGTCTCCGACTCAGTCTAACGGACCCAGCC
TTGC-3';

(SEQ ID NO: 6)
5'-CACTACGCCTCCGCTTTCCTCTCTATGGGCAGTCGGTGATCCAGCC
TTGC-3';
```

-continued

```
                                              (SEQ ID NO: 9)
5'-TCTAACGGACCCAGCCTTGCNNNNNNNATGTGG-3';
and (SEQ ID NO. 10)
5'-CCGCTTTCCTCTCTATGGGCAGTCGGTGATTCTAACGGACCCAGCC
TTGC-3';

(SEQ ID NO. 47)
5'-CCTCTCTATGGGCAGTCGGTGAT-3';
``` or the reverse complement of the aforementioned sequences, or a variant of one of the nucleotide sequences with at least 90% sequence identity or the reverse complement with at least 90% sequence identity.

In certain embodiments, the present disclosure provides an isolated nucleic acid sequence comprising one or more nucleic acids as described herein, or the reverse complement thereof, or a variant of the nucleic acid with at least 90% sequence identity or the reverse complement with at least 90% sequence identity.

In certain embodiments, the present invention provides an isolated nucleic acid comprising a nucleotide sequence according to any one of SEQ ID NOs 1 to 47, or the reverse complement of the aforementioned sequences, or a variant of one of the nucleotide sequences with at least 90% sequence identity, or the reverse complement thereof with at least 90% sequence identity.

Methods for producing nucleic acids are known in the art. Methods for assessing sequence identity between nucleic acids are known in the art.

In certain embodiments, the isolated nucleic acid consists of one of the following sequences:

```
                                              (SEQ ID NO: 1)
5'-CCAGCCTTGCNNNNNNNATGTGG-3';

(SEQ ID NO: 8)
5'-CCATCTCATCCCTGCGTGTCTCCGACTCAGTCTAACGGACCCAGCC
TTGC-3';

(SEQ ID NO: 6)
5'-CACTACGCCTCCGCTTTCCTCTCTATGGGCAGTCGGTGATCCAGCC
TTGC-3';

(SEQ ID NO: 9)
5'-TCTAACGGACCCAGCCTTGCNNNNNNNATGTGG-3';
and (SEQ ID NO. 10)
5'-CCGCTTTCCTCTCTATGGGCAGTCGGTGATTCTAACGGACCCAGCC
TTGC-3';
``` or the reverse complement of the aforementioned sequences, or a variant of one of the nucleotide sequences with at least 90% sequence identity or the reverse complement with at least 90% sequence identity.

Certain embodiments of the present disclosure provide a method of amplifying nucleic acid comprising using one or more nucleic acids as described herein.

Certain embodiments of the present disclosure provide a kit comprising one or more nucleic acids as described herein.

Certain embodiments of the present disclosure provide a system using a method as described herein.

Standard techniques and equipment may be used for recombinant DNA technology, oligonucleotide synthesis, molecular biology and enzymatic reactions. The foregoing techniques and procedures may be generally performed according to methods known in the art and/or as commercially available, and are as described for example in Sambrook et al. Molecular Cloning: A Laboratory Manual (4th ed., Cold Spring Harbor Laboratory Press, Cold Spring Harbor, N.Y. (1989)) and Ausubel et al Current Protocols in Molecular Biology (2003) John Wiley & Sons, both of which are herein incorporated by reference.

The present disclosure is further described by the following examples. It is to be understood that the following description is for the purpose of describing particular embodiments only and is not intended to be limiting with respect to the above description.

EXAMPLE 1

Generalised Protocol, Kits & Products

A generalised protocol, utilising various kits, components and instructions, for conducting DNA barcoding is as follows:

1. Kit Contents

A kit for amplification may contain the following components:
PCR-grade $H_2O$
Cell Lysis Enzyme
Cell Lysis Buffer
WGA Polymerase
WGA PCR Buffer
WGA Primer 2. Overview of Protocol Whole Genome Amplification (WGA) can be used to generate representative amplification of total DNA from single cells, small numbers of cells or their DNA equivalent. WGA reproducibly amplifies total DNA from single cells to produce microgram quantities of amplified DNA. The protocol can be used successfully on cellular, cell-free and purified genomic DNA inputs.

Use of a variety of different WGA primers is possible. Examples of WGA primers include primers which have a part of their nucleotide sequence that allows the possibility of more than one base at a particular position, and primers that can form base pairs with one or more other bases.

The protocol involves the following general steps:

(i) Sample Collection

Place the sample into a PCR tube in <2 μl of transfer buffer (eg PBS, TM)
Mark the sample location on the tube (ii) Lysis Add 3 μl of lysis solution above the sample
Tap the PCR tube to allow the lysis solution to roll over the sample
Incubate for 15 min according to the lysis program It will be appreciated that under some circumstances the cell lysis step may be omitted, permitting, for example, use of the protocol on cell-free DNA, or that the protocol may be achieved by directly entering the amplification protocol using a cell(s) and not having a discrete lysis step prior to the amplification.

(iii) Whole Genome Amplification and Target Sequence Enrichment (If Required)

Add 22 µl of PCR master mix to the lysed sample
PCR using the WGA PCR program and target specific primers
Assess WGA by agarose gel electrophoresis

3. Input Specifications (i) Number of Cells

The protocol described here is suitable for single cells or its DNA equivalent, as well as small numbers of cells (e.g. <10 cells).

(ii) Cell Collection Method

Flow sorting, microfluidics, dilution and micromanipulation are collection methods compatible with the protocol. Single cells should be transferred to a PCR tube with minimal transfer buffer (<2 µl). The location of the cell in the tube should be marked with a dot on the outside of the tube using a permanent marker pen so as to enable easy cell location for the lysis step.

(iii) DNA Dilution

It is recommended that DNA is diluted to a final concentration of 30 pg/µl in 10 mM Tris-HCl (pH 8.0) (No EDTA).

(iv) Compatible Buffers

Recommended cell transfer buffers include 10 mM Tris-HCl (pH 8.0) (No EDTA) and PBS ($Mg^{2+}$, $Ca^{2+}$ free and BSA free).

4. Protocols: Amplification (i) Cell Lysis

In this optional step, cells are lysed and DNA is made soluble with the addition of a Cell Lysis Mix and a short incubation in a PCR thermocycler.

Consumables 0.2 mL or 0.5 mL sterile PCR tubes
PCR-grade $H_2O$
Cell Lysis Enzyme
Cell Lysis Buffer
Cell or DNA samples Preparation Remove PCR-grade $H_2O$ and Cell Lysis Buffer from storage and thaw to room temperature.
Remove Cell Lysis Enzyme from storage and store in a cold block at 4° C.
Mix reagents well then briefly centrifuge to collect contents at the bottom of the tube.
Calculate volumes of reagents required for the Cell Lysis Mix.

Procedure

Prepare Cell Lysis Enzyme Dilution 1 in a 4° C. cold block by combining the following reagents:

| Compound | Volume |
| --- | --- |
| PCR-grade $H_2O$ | 6.5 µl |
| Cell Lysis Enzyme | 1.0 µl |
| Total volume | 7.5 µl |

Mix well then briefly centrifuge
Prepare Cell Lysis Mix in a 4° C. cold block for the required number of reactions by combining the following reagents:

| Component | Volume for 1 lysis reaction |
| --- | --- |
| PCR-grade $H_2O$ | 2.7 µl |
| Cell Lysis Buffer | 0.15 µl |
| Cell Lysis Enzyme Dilution 1 | 0.15 µl |
| Total volume | 3.0 µl |

Steps for Lysing Single Cells/Multi Cell Samples (a) Add 3 µl of Cell Lysis Mix above the cell sample located in a PCR tube. Make sure that the lysis mix rolls over the sample location as marked on the tube by gently tapping the tube on the benchtop. Do not mix or vortex.
(b) Briefly spin in a mini centrifuge if required to collect contents at the bottom of the tube.
(c) Repeat with other samples.

Steps for No Template Control (NTC) Preparation (a) Add 3 µl of Cell Lysis Mix to 1 sterile PCR tube labelled NTC.
(b) Add 1 µl of PCR-grade H2O to the tube labelled NTC.
Steps for DNA Sample Preparation Prior to WGA PCR (If Required):
(a) Add 3 µl of Cell Lysis Mix to the required number of sterile empty PCR tubes.
(b) Add 1 µl of 30 pg/µl DNA sample to each tube containing Cell Lysis Mix. Proceed to next step.
Incubate all samples and NTC in a thermocycler programmed as follows:

| Process | Temperature | Duration | Cycles |
| --- | --- | --- | --- |
| Lysis | 75° C. | 10 min | 1 |
| Heat inactivation | 95° C. | 5 min | |
| | 4° C. | Hold | |

Place the lysed samples in a cold block.

(ii) Whole Genome Amplification and Target Sequence Enrichment (If Required)

In this step a master mix is created and added to the lysed samples before Degenerate Oligonucleotide Primed (DOP) PCR based WGA. This generates representative amplification of total DNA from cells or their DNA equivalent. Between the low and high stringency PCR cycles, target specific primers and/or linked marker primers are added to facilitate targeted amplification of regions of interest. This provides Target Sequence Enrichment.

Consumables 1.5 mL sterile tube
PCR-grade H$_2$O
WGA PCR Buffer
WGA Primer
WGA Polymerase
Lysed samples and NTC (from Cell Lysis)
Target Specific or Linked Marker Primers (if target sequence enrichment is to be performed).

Preparation

Dilute Target Specific Primers or Linked Marker Primers to the required concentration in user supplied PCR-grade H2O.
For multiplexing Target Specific Primers or Linked Marker Primers combine all primers in equal volumes in a single primer pool.
Remove PCR-grade H2O, WGA PCR Buffer and WGA Primer from storage and thaw to room temperature.
Remove WGA Polymerase from storage and store in a cold block at 4° C.
Mix reagents well then briefly centrifuge to collect contents at the bottom of the tube.
Calculate volumes of reagents required for the WGA master mix. Enough WGA master mix should be prepared for all samples and 1 NTC plus 1-2 reactions extra. Do not add the Sequence-Specific Primers or Linked Marker Primers to this mastermix.

Procedure

Prepare WGA master mix for the required number of reactions by combining the following reagents in a 1.5 mL sterile tube in the order they are listed below:

| Component | Volume for 1 WGA reaction |
|---|---|
| PCR-grade H$_2$O | 6.5 µl |
| WGA PCR Buffer | 12.5 µl |
| WGA Primer | 2.5 µl |
| WGA Polymerase | 0.5 µl |
| Total volume | 22 µl |

Mix well then briefly spin down in a mini centrifuge.
Transfer 22 µl of WGA master mix to the individual tubes containing lysed template (sample or NTC in Cell Lysis Mix). To prevent removal of any DNA from the lysed sample, do not insert the pipette tip into the lysed sample mix. Do not mix or vortex the PCR tubes. Briefly centrifuge or spin in a mini centrifuge to collect the contents at the bottom of the tube.
(If required for genomic DNA amplification) Transfer 22 µl of WGA master mix to the individual tubes containing DNA template in Cell Lysis Mix. To prevent removal of any DNA from the sample, do not insert the pipette tip into lysed sample mix. Mix well then briefly centrifuge to collect contents at the bottom of the tube.

Incubate all samples and NTC in a thermocycler programmed as follows:

| Step | Temperature | Duration | Cycles |
|---|---|---|---|
| Initial denaturation | 95° C. | 5 min | 1 |
| Denaturation | 98° C. | 20 sec | 8 |
| Annealing | 25° C. | 1 min 30 sec | |
| Extension | Ramp to 72° C. | 1° C./4 sec | |
| | 72° C. | 1 min | |
| Cooling | 4° C. | Hold | |
| Add sequence specific primers to samples according to protocol step 6. Continue PCR program | | | |
| Denaturation | 98° C. | 20 sec | 21 |
| Annealing | 58° C. | 1 min | |
| Extension | 72° C. | 1 min | |
| Final extension | 72° C. | 1 min | 1 |
| Cooling | 15° C. | Hold | |

At the HOLD step during the PCR program, transfer 2.8 µl of the target specific primer pool to each tube containing the DNA template in the WGA PCR mix, including the NTC. To prevent removal of any sample DNA, do not insert the pipette tip into the sample mix. Instead, pipette the primers onto the side of the PCR tube, just above the sample master mix level.
Briefly centrifuge to collect contents at the bottom of the tube.
Resume the WGA with TSE PCR program.
On completion of the PCR, store the DNA either at 4° C. short term or −20° C. longer term, or proceed directly to step 4.6 WGA Quality Control.

(iii) WGA Quality Control

To confirm amplification of the DNA sample and to check for contamination in the NTC, run an agarose gel.

Consumables

Gel Loading Buffer
DNA Ladder 100-3000+bp (Geneworks DMW-100M)
Agarose
0.5× TBE
WGA products
Gel Red (Biotium 41003)

Preparation

Create and pour a 1% agarose gel by combining 1 g agarose, 100 mL 0.5× TBE and 5 µL Gel Red. Adjust the volumes to suit the size of your electrophoresis system.

Procedure

1. Apply 2 µl of PCR product in gel loading buffer to the gel.
2. Load DNA Ladder.
3. Electrophorese for ~30 min at 100 volts.

Figure 2:
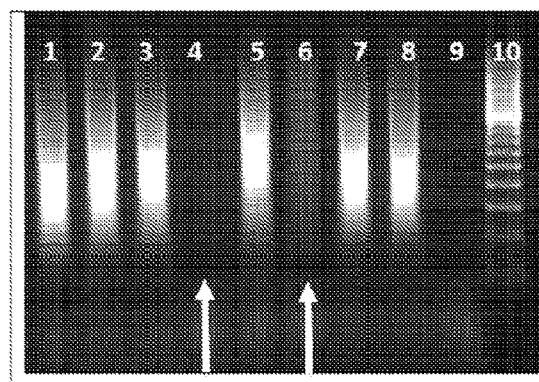
FIG. 2 shows gel electrophoresis of WGA DNA samples. Lanes 1, 2, 3, 5, 7, 8: Amplified single cells; Lane 4: Failed WGA reaction; Lane 6: Poor WGA reaction; Lane 9: NTC; Lane 10: DNA Ladder (100 bp).

Steps to Determine Quality of WGA DNA a. The WGA amplification products should appear as a smear, ranging in size from approximately 200 bp-2000 bp. The NTC should appear clean, with the presence of primer dimers (See FIG. 1).
b. TSE amplified samples typically have a slightly lower PCR yield compared to standard DOPlify® kit WGA samples. This is because the target specific primers have a small inhibitory effect on the WGA.

c. A failed WGA amplification is indicated by the presence of primer dimers, but no evidence of the larger amplification products (see FIG. 2, lane 4). Possible causes are that the sample was not successfully transferred to the PCR tube or that the sample was located in the PCR tube above the lysis and PCR reagents. Failed samples should be discarded.

d. Poor WGA amplification is indicated by smears with lower intensity or with PCR products that are notably larger or smaller than the expected size range observed for the other samples on the same agarose gel (see FIG. 2, lane 6). It is recommended that these samples are discarded but if this is not possible, the results from these samples should be interpreted with caution because they are more likely to provide false positive results due to the poorer template amplification.

Steps to Confirm Enrichment of Target Region of Interest

Depending on the end-point analysis for WGA-TSE samples, if using gene-specific PCR and electrophoretic sizing of PCR products, it may be necessary to dilute the WGA-TSE DNA sample to a concentration lower than the typical recommended input concentration for the PCR. Due to the enrichment of the target sequence in the WGA, using the standard recommended DNA concentration can result in the appearance of additional weakly amplified PCR products that are probably generated from incomplete DNA fragments. To reduce electrophoretic banding of these partial PCR products, titrate the WGA TSE sample concentrations for the end-point assay. Typically this should be performed in the range of 1:20-1:10 of the template standard concentration.

a. Confirm sequence enrichment using semi-quantitative target specific PCR (where a low number of PCR cycles are used so that the target band is just visible on a gel) of WGA+TSE compared to WGA only as the PCR template (see FIG. 3, lane 2-5 vs lane 6-9). Do not run the PCR to plateau phase. Alternate methods can also be used; e.g. a nested PCR directed towards the target regions can be used to confirm that the target sequence enrichment has occurred.

b. WGA+TSE DNA and the sequence-specific PCR products generated using it as a template are compatible with a range of methods including next generation sequencing (NGS), PCR, electrophoresis & Sanger sequencing.

c. To increase the depth of coverage of enriched sequence for NGS analysis, the sequence-specific PCR product can be pooled with the WGA+TSE DNA and barcoded as a single sample. The sequence-specific PCR product or products can be diluted with the DNA in a range of 1:20 to 1:1 depending on the depth of coverage required for NGS analysis. Sequencing can then be performed following the standard PG-Seq™ kit protocol or similar.

(iv) Optimisation of the TSE Protocol Sequence-Specific Primer Concentration

It is recommended that you optimise the concentration of specific individual or multiplex primers to add to the DOPlify® for the TSE protocol using 30 pg gDNA as template prior to using the TSE protocol on test samples. This only needs to be done once and the same concentration can be used for all subsequent TSE amplifications with that primer set. This process needs to be performed for each individual or multiplex primer set.

The following protocol is to be used as a guide for the primer concentration optimisation.

Cell Lysis

1. Label 11 sterile empty PCR tubes with the following labels:

| Tube Label |
| --- |
| A-1 |
| B-1 |
| C-2 |
| D-2 |
| E-5 |
| F-5 |
| G-10 |
| H-10 |
| I-0 |
| J-0 |
| K-NTC |

2. Prepare enough Cell Lysis Mix for 12 samples according to the DOPlify® kit TSE protocol.
3. Add 3 µl of Cell Lysis Mix to the sterile empty PCR tubes.
4. Add 1 µl of 30 pg gDNA diluted in PBS or PCR-grade $H_2O$ to each tube except the NTC.
5. Add 1 µl of PCR-grade $H_2O$ to the NTC.
6. Incubate all tubes in a thermocycler according to the program: RHS Lysis.

Whole Genome Amplification and Target Sequence Enrichment

1. Dilute all forward and reverse sequence-specific primers and pool all primers in equal volumes if primers are being multiplexed. Note that the concentration of each primer set to add to the multiplex can be further optimised by comparing the amount of sequence-specific product generated in step 8 below. Dilute the primer pool to working stock concentrations of 1 µM, 2 µM 5 µM and 10 µM with PCR-grade $H_2O$.
2. Prepare enough WGA mastermix for 12 samples according to the DOPlify® kit TSE protocol. Note that the sequence-specific primers are not added to this mastermix.
3. Transfer 22 µl of WGA mastermix to the 11 tubes. There will be WGA mastermix left over that is discarded.
4. Incubate all tubes in a thermocycler according to the program: RHS WGA with TSE (page 10).
5. At the hold step during the PCR program, add 2.8 µl of the corresponding sequence-specific primer dilution to each tube.

| Tube Label | TSE Primer addition |
| --- | --- |
| A-1 | 2.8 uL of 1 µM pool |
| B-1 | 2.8 uL of 1 µM pool |
| C-2 | 2.8 uL of 2 µM pool |
| D-2 | 2.8 uL of 2 µM pool |
| E-5 | 2.8 uL of 5 µM pool |
| F-5 | 2.8 uL of 5 µM pool |

-continued

| Tube Label | TSE Primer addition |
|---|---|
| G-10 | 2.8 uL of 10 μM pool |
| H-10 | 2.8 uL of 10 μM pool |
| I-0 | 2.8 uL of PCR-grade H$_2$O |
| J-0 | 2.8 uL of PCR-grade H$_2$O |
| K-NTC | 2.8 uL of PCR-grade H$_2$O |

Figure 3:
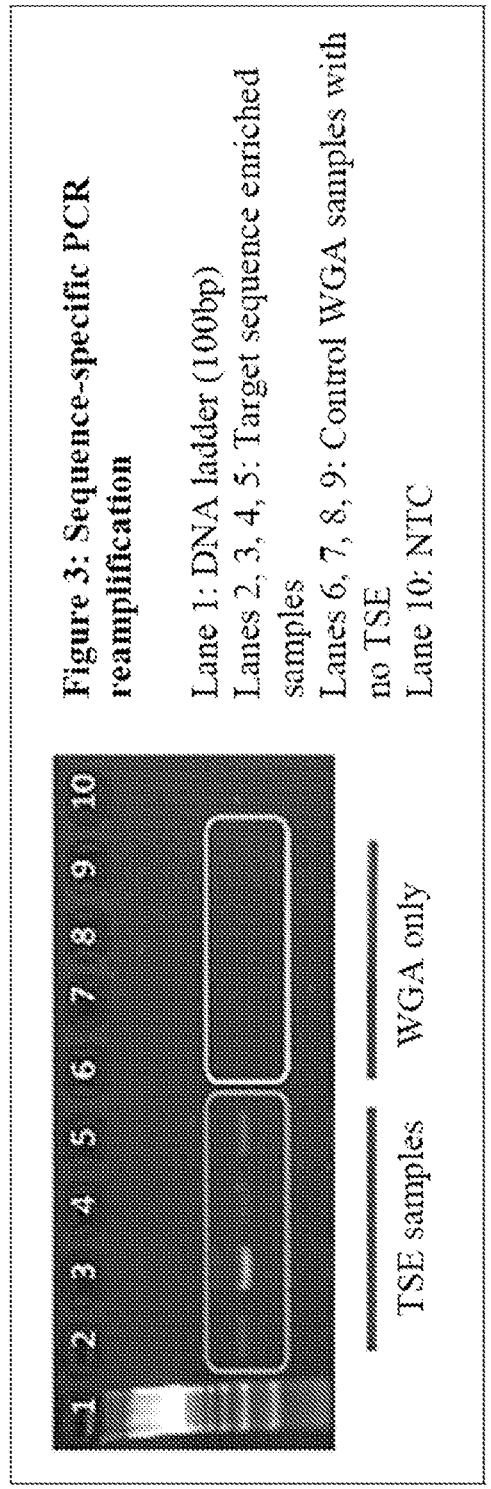
FIG. 3 shows gel electrophoresis of semi-quantitative second round target specific PCR generated products after combined WGA and TSE single cell products were seeded into a target specific PCR. Enriched amplification of the target D4S43 marker was achieved due to the addition of 0.5 uM D4S43 target specific primers (green circle, lanes 2-5) compared with the control (WGA only) (yellow circle, lanes 6-9).
Figure 4:
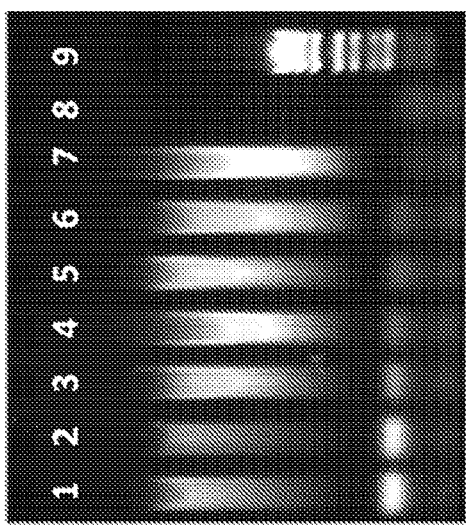
FIG. 4 shows gel electrophoresis of WGA DNA samples with TSE using different target specific primer concentrations. Lanes 1, 2: 10 µM; Lanes 3, 4: 5 µM; Lanes 5, 6: 2.5 µM; Lane 7: Control WGA sample with no TSE primers; Lane 8: NTC; Lane 9: DNA ladder.

6. Resume the RHS WGA with TSE PCR program.
7. To confirm amplification of the DNA sample and determine the optimal concentration of target specific primers to add for TSE, run an agarose gel. Compare the yield of the WGA PCR with TSE samples to the control samples with no sequence-specific primers added I-0 and J-0 (FIG. 4).
8. To evaluate the enrichment of your target sequence, perform a PCR with the same sequence-specific primers and use DNA from each of the WGA TSE PCRs as the template (tubes A-1, B-1, C-2, D-2, E-5, F-5, G-10 H-10, I-0 and J-0). If necessary, dilute each WGA TSE amplicon sample (approximately 1:20-1:10 as a guide) or use neat as a template for sequence-specific PCR amplification.
9. The optimal concentration of sequence-specific primers will be the highest concentration that has minimal impact on WGA yield and generates detectable PCR product in the second sequence-specific PCR using the WGA TSE amplicons as template (FIG. 3).

EXAMPLE 2

PCR Barcoding Using Barcoded Adapter Primer

Figure 5:
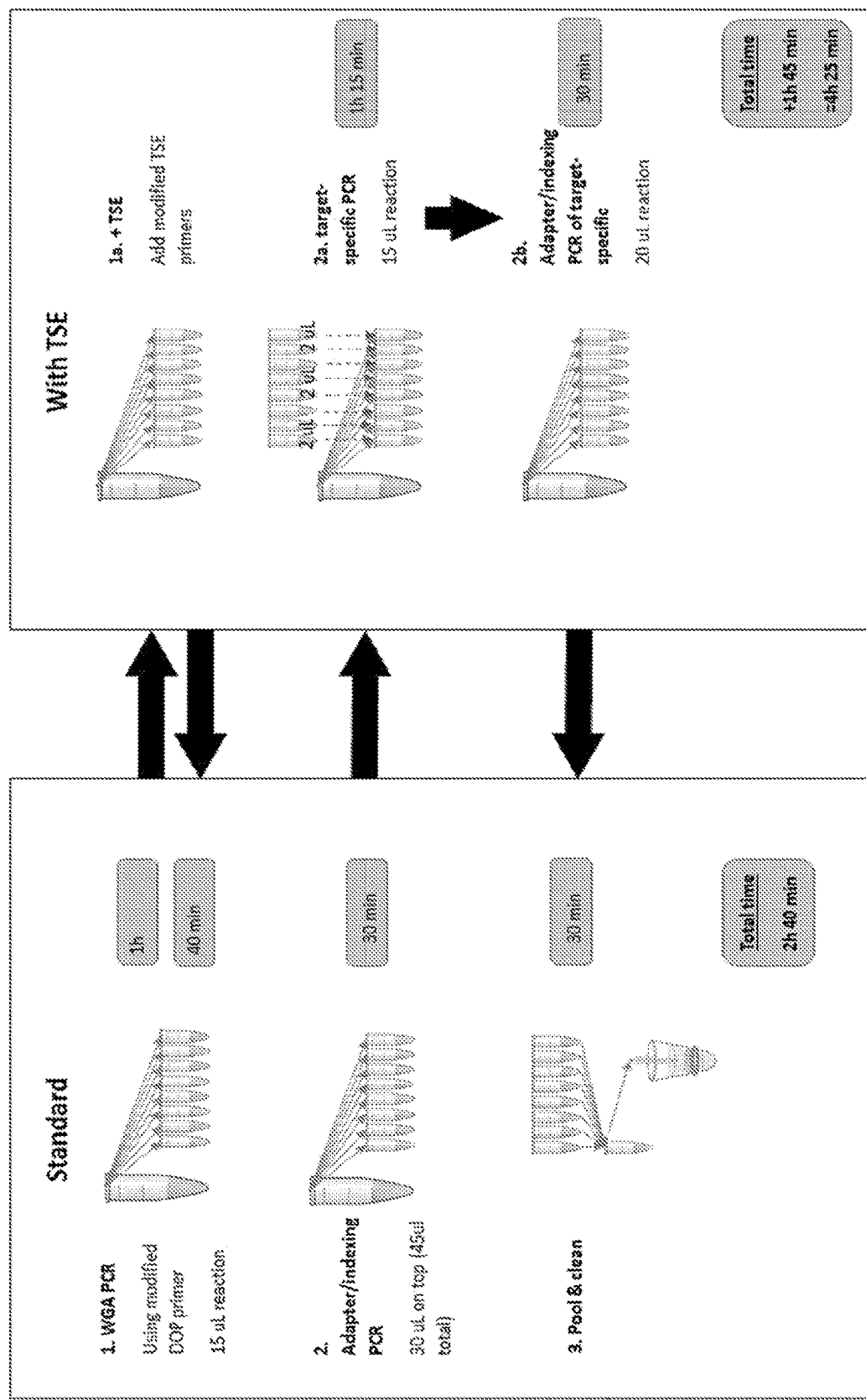
FIG. 5 shows a schematic representation of a first work flow of PCR barcoding with target sequence enrichment, according to a first embodiment of the present disclosure.

A schematic representation of a first work flow according to a first embodiment is provided in FIG. 5, showing barcoding using the protocol as described herein (left panel) or incorporating target specific enrichment in the side panel to the right.

Primer sequences used are shown in FIG. 6.

Step 1—WGA PCR

5'-CCAGCCTTGCNNNNNNNATGTGG-3' (SEQ ID NO: 1)—Amplifying primer with a degenerate nucleotide sequence (, where N is any nucleotide) and a 5' fixed sequence (CCAGCCTTGC (SEQ ID NO: 2)).

Step 2—Adapter/Barcoding PCR

5'CCATCTCATCCCTGCGTGTCTCCGACTCAG<barcode>CCAGCCTTGC-3'. A first primer comprising the 5' fixed nucleotide sequence (5'-CCAGCCTTGC-3' (SEQ ID NO: 2)), a specific identifier sequence of choice ("barcode"; 5'-TCTAACGGAC-3' SEQ ID NO: 3) and an adapter sequence for subsequent priming of DNA synthesis ("A-adapter"; 5'-CCATCTCATCCCTGCGTGTCTCCGACTCAG-3' (SEQ ID NO: 4)). The entire primer sequence in this embodiment is 5'-CCATCTCATCCCTGCGTGTCTCCGACTCAGGATTCTAACGGACCCAGCCTTGC-3' (SEQ ID NO: 5).

5'-CACTACGCCTCCGCTTTCCTCTC-TATGGGCAGTCGGTGATCCAGCCTTGC-3' (SEQ ID NO: 6)—A second primer comprising the 5' fixed nucleotide sequence ('-CCAGCCTTGC-3' (SEQ ID NO: 2)) and an adapter sequence ("P1-adapter"; 5'-CACTACGCCTCCGCTTTCCTCTCTATGGGCAGTCGGTGAT-3' (SEQ ID NO: 7)).

The workflow is shown in FIGS. 5 and 7.
For target specific enrichment (TSE), as shown in Step 1a in FIG. 5, the primer sequences are as follows:

5'-CCAGCCTTGC<forward target-specific sequence>-3'—A forward TSE primer comprising the 5' fixed nucleotide sequence (CCAGCCTTGC (SEQ ID NO: 2), and a forward target-specific sequence, being a sequence that is identical or almost identical, or complementary to, a sequence flanking a target region.

5'-CCAGCCTTGC<reverse target-specific sequence>-3'—A reverse TSE primer comprising the 5' fixed nucleotide sequence (CCAGCCTTGC (SEQ ID NO: 2), and a reverse target specific sequence, being a sequence that is identical or almost identical, or complementary to, a sequence flanking a target region, on a complementary strand to the forward target specific sequence.

For target sequence enrichment (TSE), as shown in Step 2a in FIG. 5, the forward and reverse primer sequences are the same as for use in Step 1a.

Figure 9:
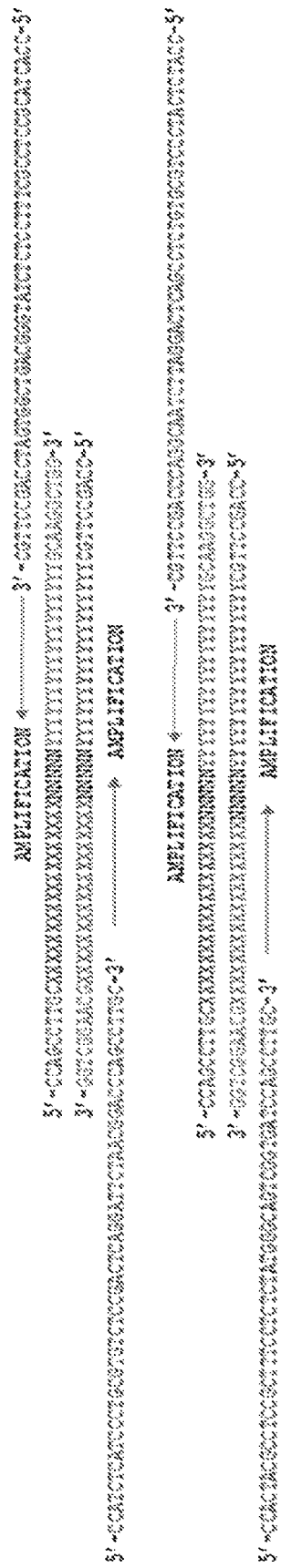
FIG. 9 shows primers used for target sequence enrichment in a first work flow of PCR barcoding, and examples of expected PCR products, according to a first embodiment of the present disclosure.

The workflow for TSE is shown in FIGS. 5, 8 and 9.

Primer sequences for TSE steps 1a (TSE), 2a (target region specific PCR) and 2b (adapter/barcoding PCR of TSE product) are shown in FIGS. 8 and 9.

5'-CCATCTCATCCCTGCGTGTCTCCGACTCAGTCT-AACGGACCCAGCCTTGC-3' (SEQ ID NO: 8) being the first primer comprising the 5' fixed nucleotide sequence (CCAGCCTTGC (SEQ ID NO: 2)), a specific identifier sequence of choice ("barcode", 5'-TCTAACGGAC-3' (SEQ ID NO: 3)) and an adapter sequence for subsequent priming of DNA synthesis ("A-adapter"; 5'-CCATCTCATCCCTGCGTGTCTCCGACTCAG-3' (SEQ ID NO: 4)).

5'-CACTACGCCTCCGCTTTCCTCTC-TATGGGCAGTCGGTGATCCAGCCTTGC-3' (SEQ ID NO: 6) being the second primer comprising the 5' fixed nucleotide sequence (CCAGCCTTGC (SEQ ID NO: 2)) and an adapter sequence ("P1-adapter"; 5'-CACTACGCCTCCGCTTTCCTCTCTATGGGCAGTCGGT-GAT-3' (SEQ ID NO: 7)).

Figure 11:
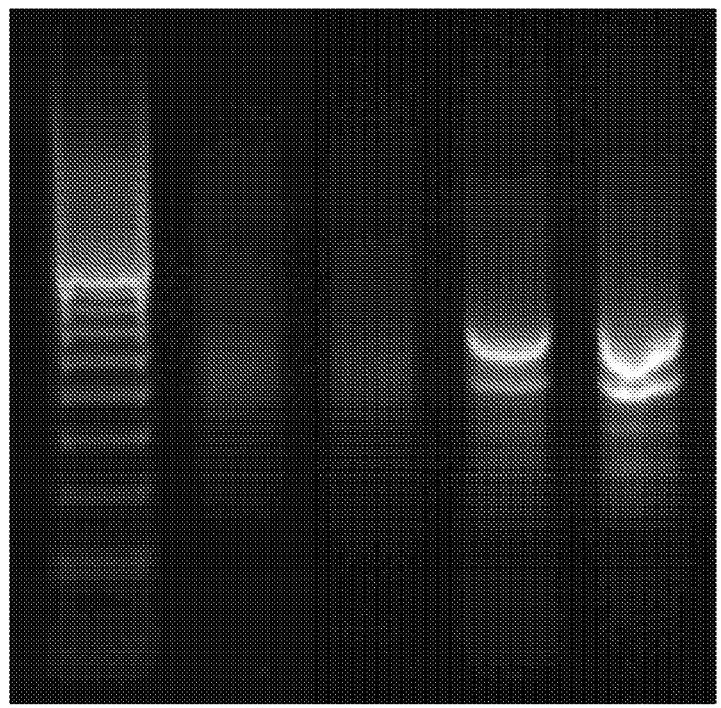
FIG. 11 shows gel electrophoresis of semi-quantitative haemoglobin subunit beta ("HBB") specific PCR. Two different DNA templates were used, (1) WGA with TSE for HBB and (2) WGA without TSE for HBB. Lane 1, pUC19 DNA marker; lane 2-3, control WGA template without TSE; and lane 4-5, template of WGA with TSE, according to a first embodiment of the present disclosure.
Figure 12:
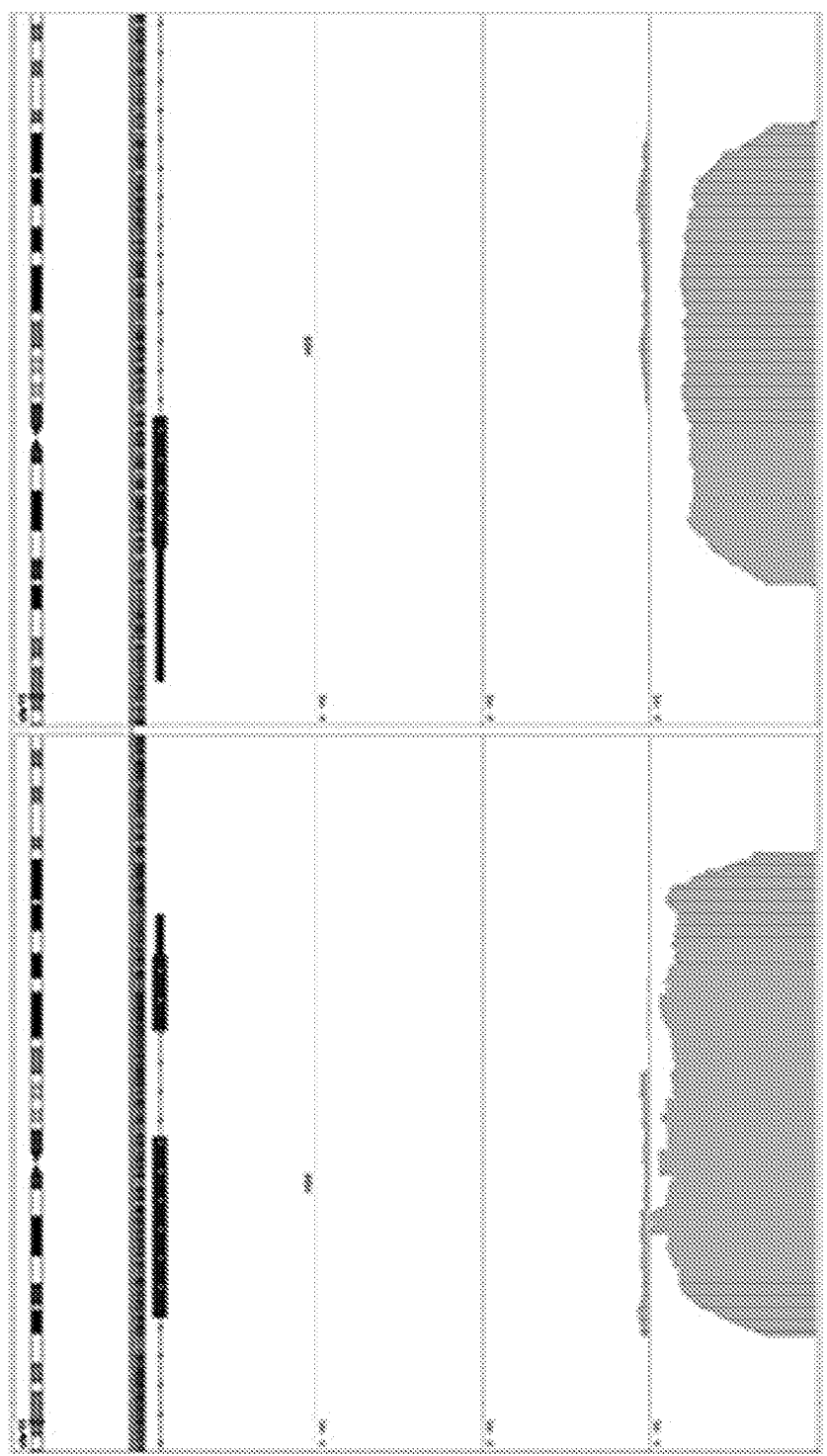
FIG. 12 shows Integrative Genomics Viewer (IGV; Robinson et al. (2011) *Nature Biotechnology* 29, 24-26; Thorvaldsdottir et al. (2013) *Briefings in Bioinformatics* 14, 178-192) screenshot of (A) HBB for WGA only sample and enrichment of target DNA during WGA with TSE or following combined WGA+TSE+HBB multiplex PCR products (1:10 dilution), prepared with an Illumina sequencing preparation and sequenced on an Illumina NGS platform, and (B) HBB for a first work flow of PCR barcoding+TSE, sequenced on a ThermoFisher NGS platform, according to a first embodiment of the present disclosure.
Figure 12:
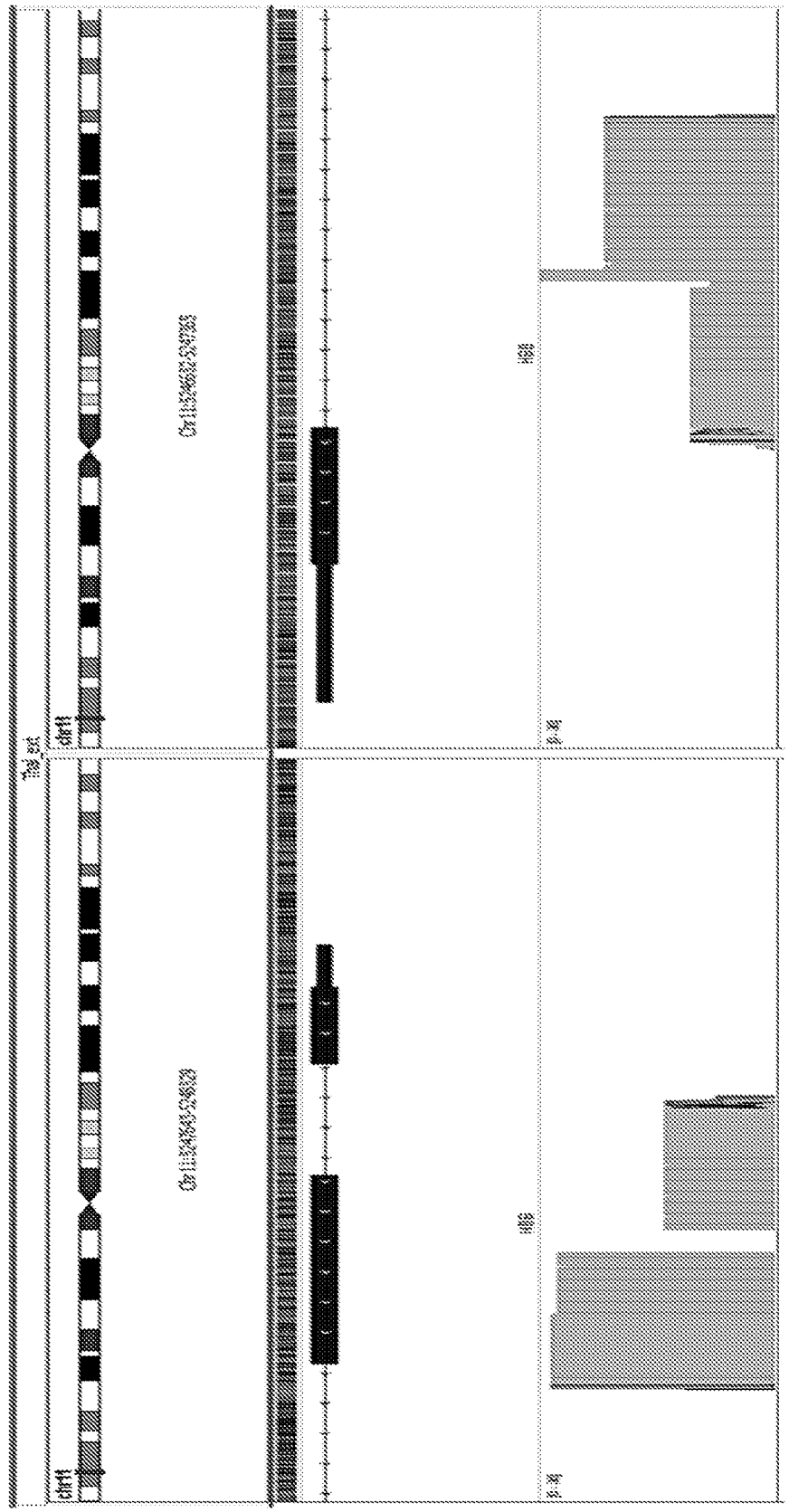

Methods 5-cell samples were manually sorted from aneuploid cell lines (Coriell Institute for Medical Research) and prepared for sequencing using a two-stage, single tube protocol as shown in FIG. 1. DNA was amplified using standard DOPlify® kit reagents and the WGA PCR Primer (FIG. 11). Subsequently, publicly available Ion Torrent™ (Thermo Fisher, US) NGS adapter sequences and barcodes were incorporated utilising a second PCR step within the same PCR tube. Incorporation of the adapter sequences (at both the 5' and 3' ends of the amplified DNA) was quantified using qPCR (Kapa Biosystems, US) with adapter sequence-specific primers (PerkinElmer Health Sciences Australia Pty Ltd), providing a library viability score.

Figure 10:
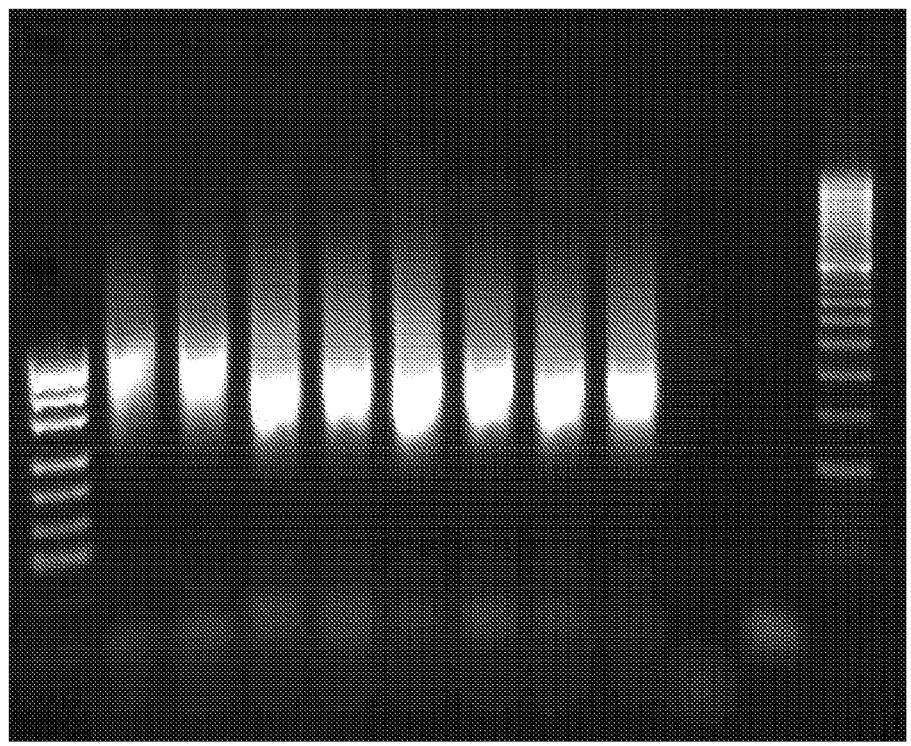
FIG. 10 shows gel electrophoresis of samples prepared by PCR barcoding and subsequently sequenced to produce results shown in FIG. 9, according to a first embodiment of the present disclosure.

FIG. 10 shows a 1% agarose gel electrophoresis of the samples, prepared by an embodiment of the PCR barcoding method, that were sequenced. Lanes 2 & 3 are with TSE protocol.

FIG. 11 shows a 1% agarose gel electrophoresis of target specific PCR product using WGA only (lanes 2-3) and target sequence enriched (lanes 4-5) template using an embodiment of the target sequence enrichment work flow.

The barcoded samples were pooled and prepared for sequencing using an Ion Chef™ System (Thermo Fisher, US) and sequenced using an Ion PGM™ System. The sequencing data was bioinformatically aligned to hg19, sequencing metrics collated and the data analysed to determine sample ploidy status.

Integrative Genomics Viewer (IGV) screenshot of HBB for WGA only and WGA with target sequence enrichment samples, and PCR barcoding samples with target sequence enrichment is shown in FIG. 16.

Whole chromosome aneuploidy results from 5-cell samples were concordant with the expected karyotypes of the 47,XY,+13 (FIG. 13B) and 46,XY cell lines.

Figure 13:
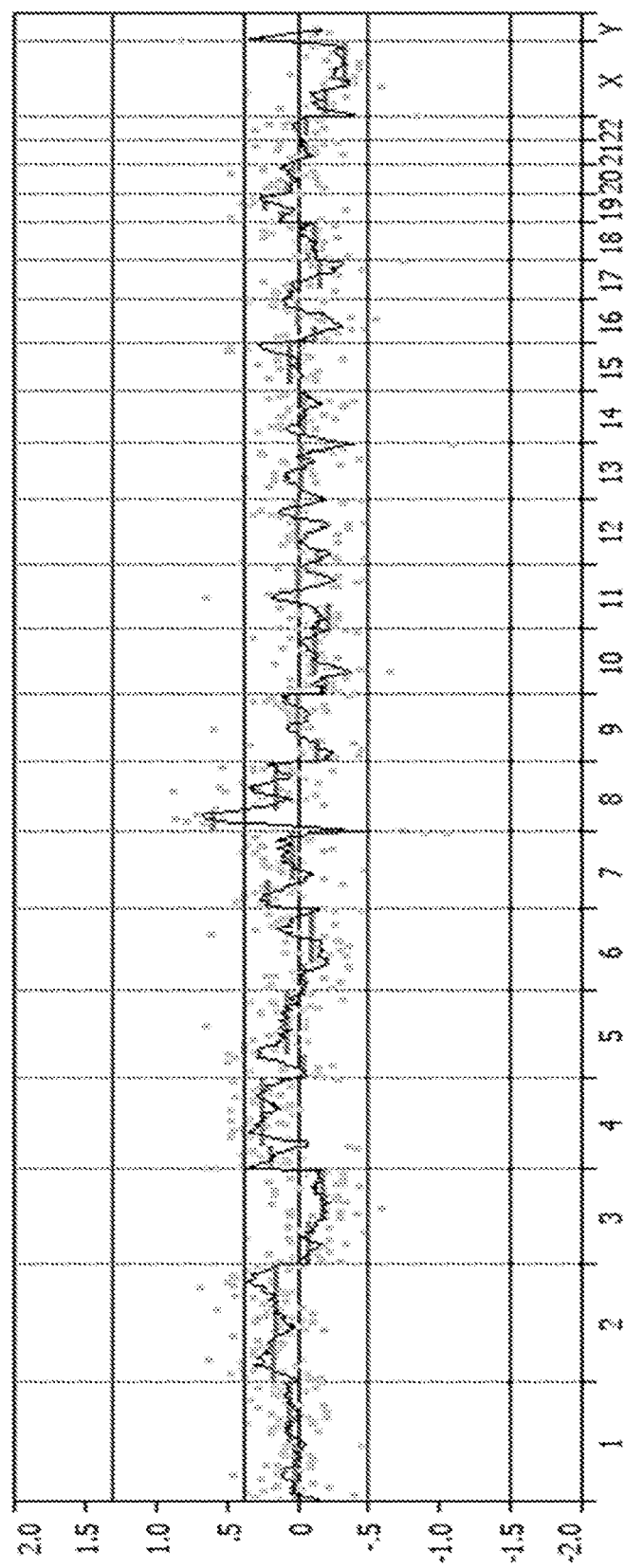
FIG. 13 shows a 5-cell sample NGS result with (A) 7 Mb deletion and 32 Mb duplication on chromosome 8 (GM14485; obtained from the NIGMS Human Genetic Cell Repository at the Coriell Institute for Medical Research) and (B) a whole duplication of chromosome 13 (GM02948B; Coriell Institute for Medical Research), according to a first embodiment of the present disclosure.
Figure 13:
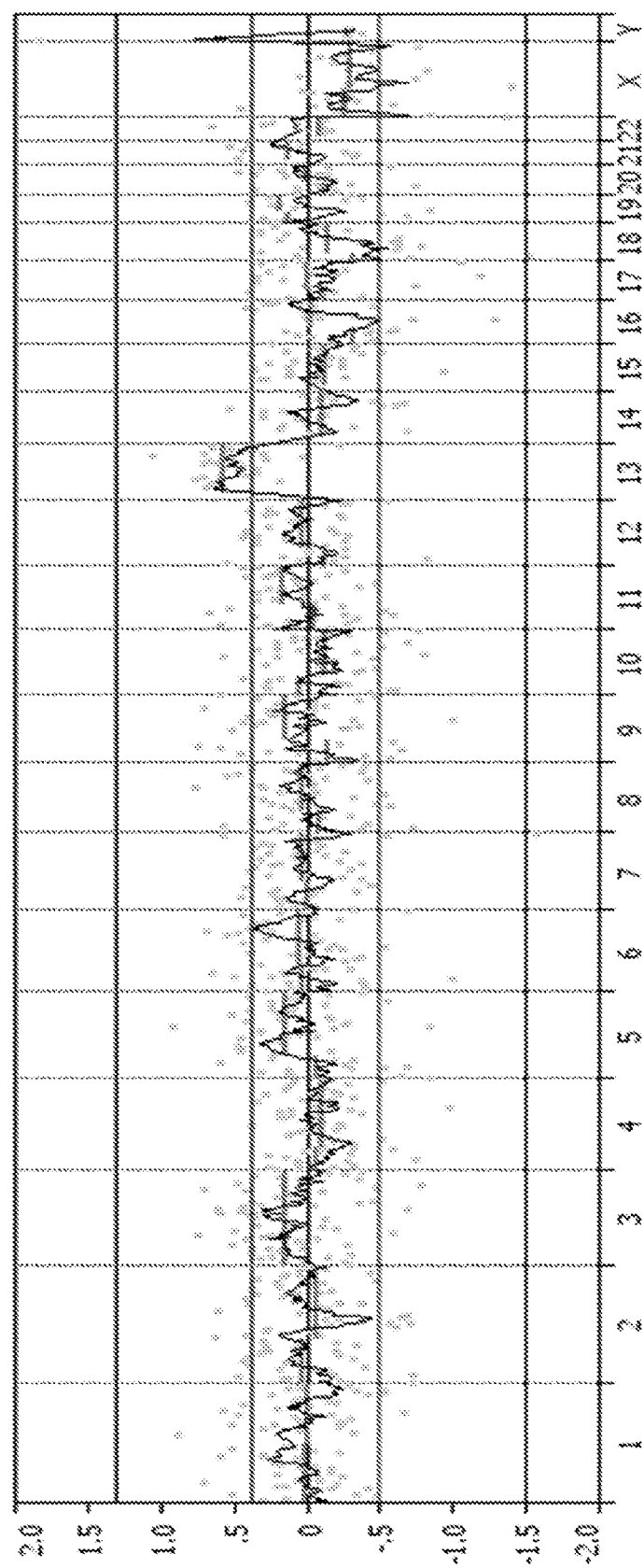

Detection of a 7 Mb deletion and 32 Mb duplication on chromosome 8 using a 5-cell sample was also concordant with the expected karyotype of the cell line used (GM14485; Coriell Institute for Medical Research) (FIG. 13A).

The average mtDNA content was 0.08-0.36%.

Conclusions

This novel method provides a single tube amplification and barcoding protocol for sequencing on Thermo Fisher (US) NGS platforms to allow rapid, scalable and economical sequencing for PGT-A, and the incorporation of the Target Sequence Enrichment protocol (PerkinElmer Health Sciences Australia Pty Ltd) for combined PGT-M & PGT-A from a single embryo biopsy.

EXAMPLE 3

PCR Barcoding Using Barcoded WGA Primer

A schematic representation of a work flow according to a second embodiment another embodiment is provided in FIG. 14. Variations of this embodiment are shown in the panels on the left and right sides.

Primer sequences used are shown in FIG. 15.

Protocols for use in this workflow are described in the previous examples.

Step 1—WGA/Barcoding PCR

5'-<barcode>CCAGCCTTGCNNNNNNATGTGG-3— Amplifying primer with a degenerate nucleotide sequence (NNNNNN, N is any nucleotide), a 5' fixed sequence (5'-CCAGCCTTGC-3' (SEQ ID NO: 2)) and a specific identifier sequence of choice ("barcode"; 5'-TCTAACGGAC-3' (SEQ ID NO: 3). The entire primer sequence in this embodiment is 5'-TCTAACGGACCCAGCCTTGCNNNNNNATGTGG (SEQ ID NO: 9).

Step 2—Adapter PCR

5'-CCATCTCATCCCTGCGTGTCTCCGACTCAGTCTAACGGACCCAGCCTTGC-3' (SEQ ID NO: 8)—A first primer comprising the 5' fixed nucleotide sequence (CCAGCCTTGC (SEQ ID NO: 2), a specific identifier sequence of choice ("barcode"; 5'-TCTAACGGAC-3' (SEQ ID NO: 3)) and an adapter sequence for subsequent priming of DNA synthesis ("A-adapter"; 5'-CCATCTCATCCCTGCGTGTCTCCGACTCAG-3' (SEQ ID NO: 4)).

5'-CCGCTTTCCTCTCTATGGGCAGTCGGTGATTCTAACGGACCCAGCCTTGC-3' (SEQ ID NO: 10)—A second primer comprising the 5' fixed nucleotide sequence (CCAGCCTTGC (SEQ ID NO: 2) and an adapter sequence which is identical or complementary to a nucleotide sequence attached to a solid substrate ("P1-adapter"; 5'-CCGCTTTCCTCTCTATGGGCAGTCGGTGAT-3' (SEQ ID NO: 11).

The workflow and primers are shown in FIGS. 14 to 16.

Figure 17:
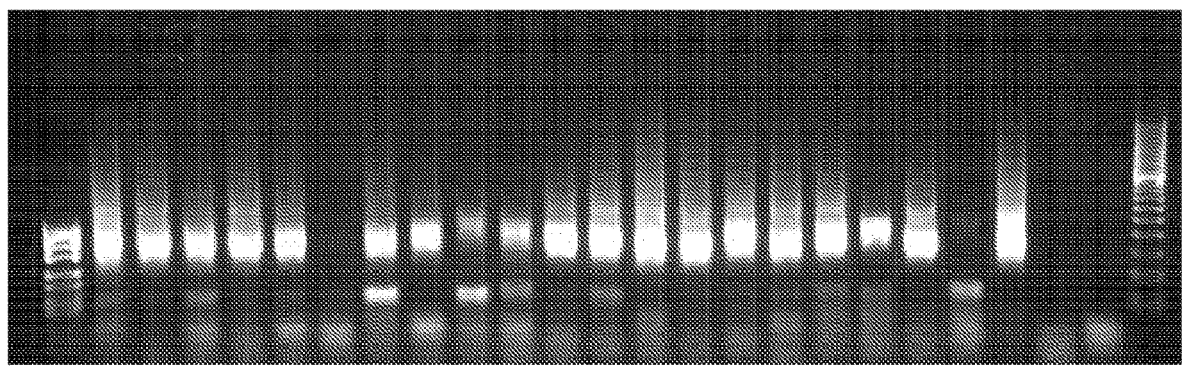
FIG. 17 shows PCR product after gel electrophoresis for an embodiment of the PCR barcoding method, according to a second embodiment of the present disclosure.

FIG. 17 shows a 1% agarose gel electrophoresis of samples prepared using an embodiment of the PCR barcoding method.

Figure 18:
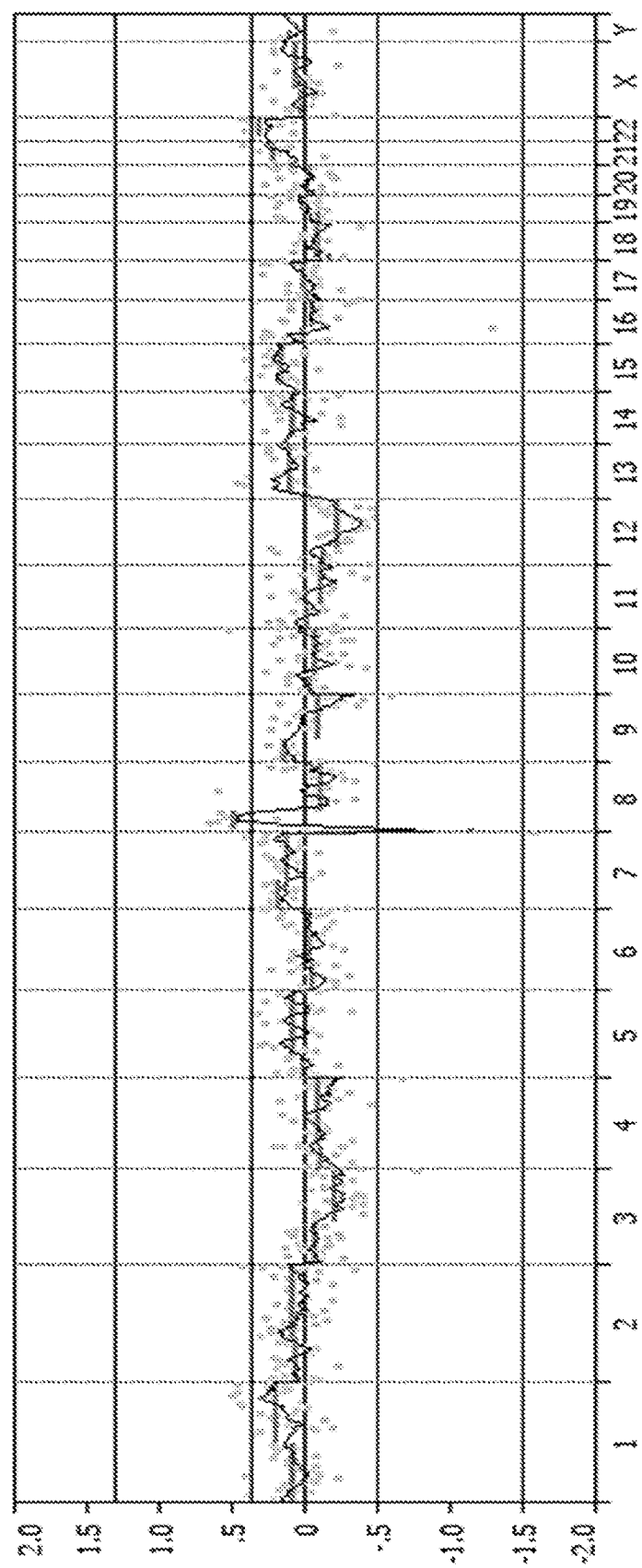
FIG. 18 shows a 5-cell sample result with (A) 7 Mb deletion and 32 Mb duplication on chromosome 8 (GM14485; Coriell Institute for Medical Research) and (B) a whole duplication of chromosome 21 and XXY aneuploidy (GM04965; Coriell Institute for Medical Research), according to a second embodiment of the present disclosure.
Figure 18:
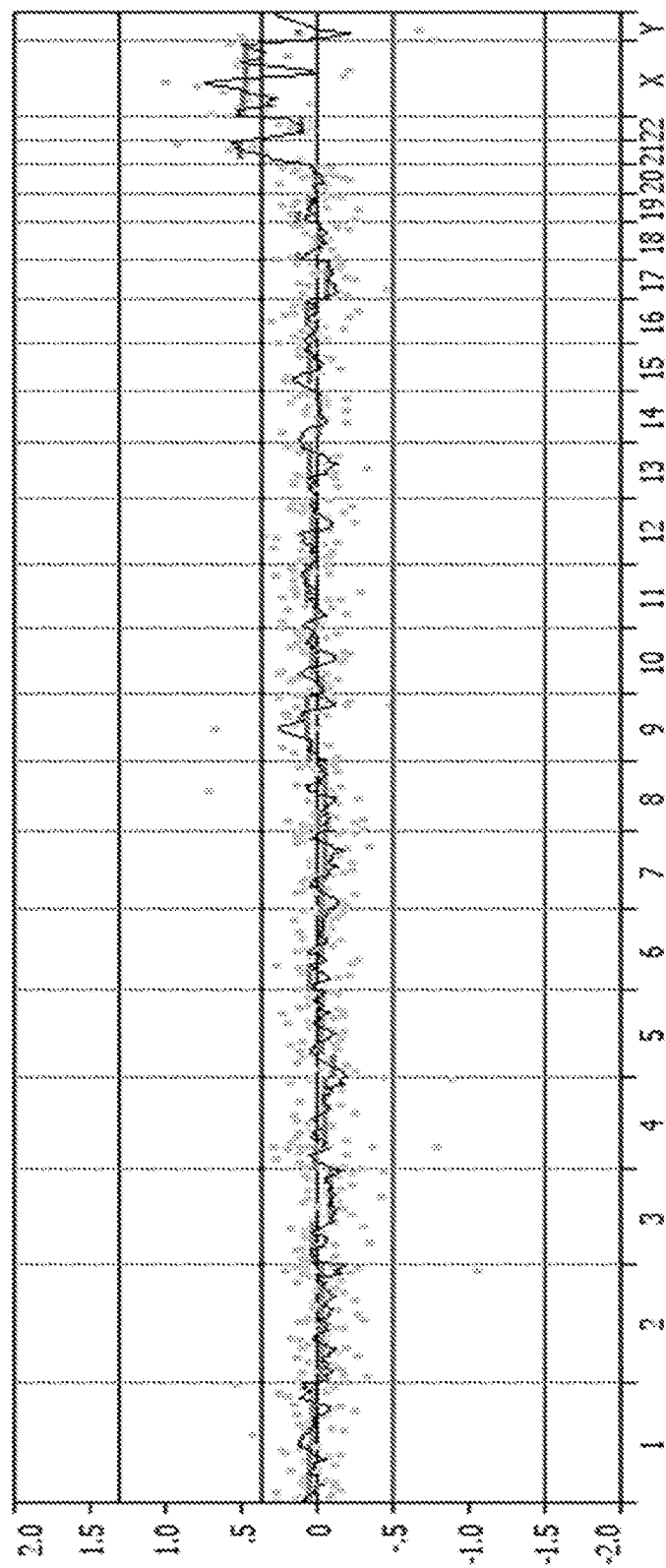

FIG. 18 shows a 5-cell sample result with (A) 7 Mb deletion and 32 Mb duplication on chromosome 8 (GM14485) and (B) a whole chromosome duplication of chromosome 21 and XXY aneuploidy (GM04965).

Conclusions

This novel method provides a single tube amplification and barcoding protocol for sequencing on Thermo Fisher (US) NGS platforms to allow rapid, scalable and economical sequencing for PGT-A, and the incorporation of the Target Sequence Enrichment protocol (PerkinElmer Health Sciences Australia Pty Ltd) for combined PGT-M & PGT-A from a single embryo biopsy.

EXAMPLE 4

DNA Barcoding is Not Efficient Using Variant Primer for WGA and Barcoding

A workflow according to a comparative example using a variant amplifying primer, and variant first and second primers is provided in FIG. 19. In this comparative example, amplification was not efficient.

Step 1—WGA PCR/Barcoding

5'-GTCTCCGACTCAG<barcode>GATNNNNNNATGTGG-3'—Amplifying primer comprising a nucleotide sequence 5'-GATNNNNNNATGTGG-3' (modified DOP-PCR; SEQ ID NO: 12) having a degenerate nucleotide sequence), a specific identifier sequence of choice ("barcode"), and part of Adapter A (5'-GTCTCCGACTCAG-3' (SEQ ID NO: 13).

Step 2—Adapter PCR

5'-CCATCTCATCCCTGCGTGTCTCCGACTCAG-3' (SEQ ID NO: 14)—A first primer comprising a truncated Adapter A including priming site.

5'-CCTCTCTATGGGCAGTCGGTGATNNNNNNATGTGG-3' (SEQ ID NO: 15)—A second primer comprising the modified DOP-PCR sequence described above and Adapter P1 sequence (5'-CCTCTCTATGGGCAGTCGGT-3' (SEQ ID NO: 16).

Figure 20:
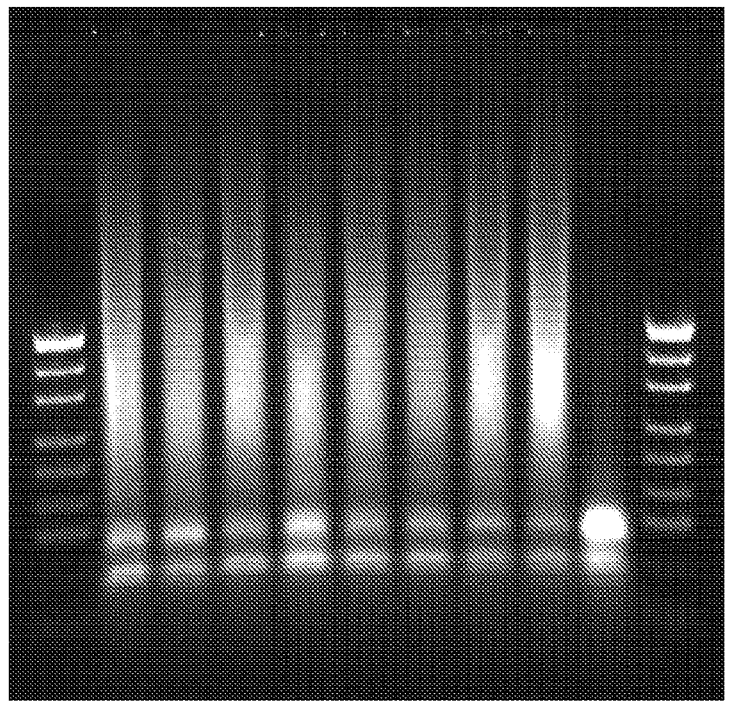
FIG. 20 shows PCR product after electrophoresis for an embodiment of the PCR barcoding method according to a comparative example.

FIG. 20 shows PCR product after electrophoresis through a 1% agarose gel for an embodiment of the PCR barcoding method.

Figure 21:
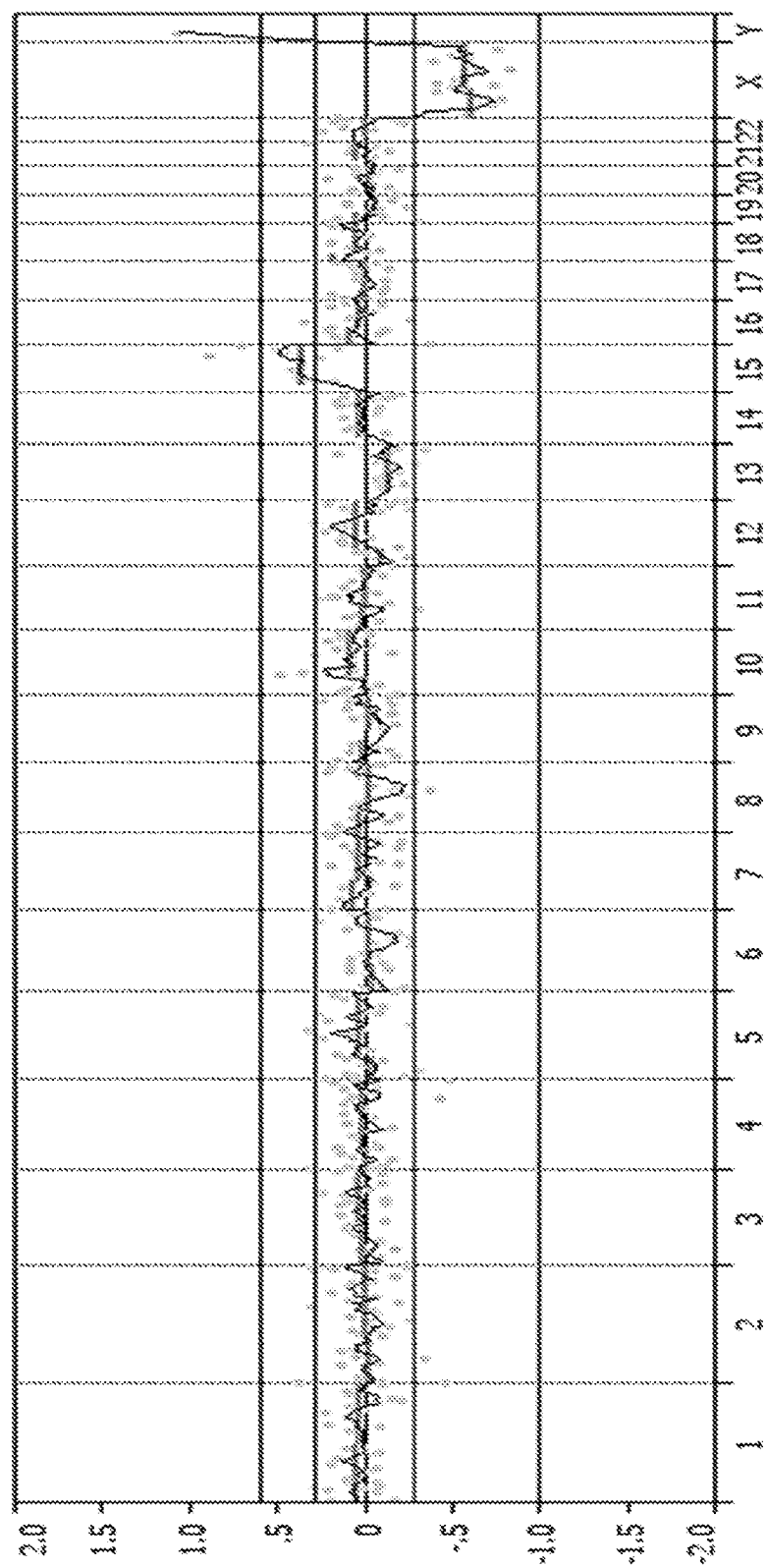
FIG. 21 shows a 5-cell sample result with (A) a whole duplication of chromosome 15 (GM07189; Coriell Institute for Medical Research) and (B) a whole duplication of chromosome 21 and XXY aneuploidy (GM04965; Coriell Institute for Medical Research) according to a comparative example.

FIG. 21A shows M4 CNV plot. Illumina library prep on barcoded PCR product. XY+15. FIG. 21B shows M4 CNV plot. Illumina library prep on barcoded PCR product. XXY+21.

This method of single-tube PCR amplification and barcoding highlights some characteristics of an inefficient protocol. The characteristics of the generated DNA library may include low DNA yield, incomplete adapter incorporation and or biased adapter incorporation.

These results demonstrate that for the barcoding of nucleic acids, the amplification using a fixed sequence 5' to a degenerate sequences on the WGA primer and on the first and second primers provides more efficient amplification NGS library preparation workflow. This allows the use of a barcode sequence to be introduced into the WGA primer and/or introduced into either or both of the first and second primer, and thereby efficiently produce nucleic acids that have been barcoded.

EXAMPLE 5

Comparative Details of Workflows

The following table shows a comparison of the methods described in Example 2, Example 3 and Example 4 after WGA PCR and clean up.

|  | ng/ul |
|---|---|
| Example 4 | 10-20 |
| Example 3 | 60-80 |
| Example 2 | 60-80 |

Comparison of the gels of FIGS. 10, 17, 20 and 21, it can be seen that Example 4 (FIG. 20) has sub-optimal product size (large range) and excess primer-dimer (although Example 3 (FIG. 17) also has excess primer-dimer). The target range for product size should be within ~200-500 bp as clonal amplification and sequencing of libraries with fragments >500 bp is problematic on some Thermo Fisher (US) NGS platforms. Size selection is an option when a library has a large range, but fragments <500 bp are still necessary for this to be valid. Product yield is much lower in Example 4 (FIG. 20), as indicated by brightness relative to the DNA marker, indicating sub-optimal PCR efficiency.

PCR incorporation of the Ion Torrent™ barcodes was successfully achieved for Examples 2 and 3.

The most efficient & versatile method (Example 2) was selected based on the differences observed for DNA yield, fragment size and library viability, as shown in the following table:

Summary of WGA PCR DNA characteristics for select methods of PCR barcoding.

|  | Method 1 | Method 2 | Method 3 |
|---|---|---|---|
| WGA DNA yield (ng/ul) | + | +++ | ++++ |
| Size range (bp) | 300-800 | 280-680 | 300-700 |
| Library viability | + | +++ | ++ |

The most time efficient protocol produced amplified, sequencing ready samples within 3 hours including clean-up time, with a hands-on time of approximately 1 hour.

Conclusions

The novel method described herein provides a single tube amplification and barcoding protocol for sequencing on Thermo Fisher (US) NGS platforms to allow rapid, scalable and economical sequencing for PGT-A, and the incorporation of the Target Sequence Enrichment protocol (PerkinElmer Health Sciences Australia Pty Ltd) for combined PGT-M & PGT-A from a single embryo biopsy.

EXAMPLE 6

PCR Barcoding Using Barcoded Amplifying Primer v2

A schematic representation of another work flow according to a further embodiment is provided in FIG. 22.

Protocols for use in this workflow are described in the previous examples.

Step 1—WGA PCR

5'-GCTCTTCCGATCTACTCGAGNNNNNNATGTGG-3' (SEQ ID NO: 17)—Amplifying primer with a degenerate nucleotide sequence (5'-NNNNNN-3') and a 5' fixed sequence (5'-GCTCTTCCGATCTACTCGAG-3' (SEQ ID NO: 18)).

Step 2—Adapter/Barcoding PCR

5'-AATGATACGGCGACCACCGAGATCTA-CACTCTTTCCCTACACGACGCTCTTCCGA TCTACTCGAG-3' (SEQ ID NO: 19)—A 3' that includes a sequence that is identical to the 5' fixed nucleotide sequence (5'-ACACTCTTTCCCTACACGACGCTCTTCCGATC-TACTCGAG-3' (SEQ ID NO: 48)) of the amplifying primer and a P5 read sequence that it is identical or complimentary to a P5 read sequence primer and a P5 adapter sequence (5'-AATGATACGGCGACCACCGAGATCT-3' (SEQ ID NO: 49)) that is identical or complimentary to a P5 sequence attached to a solid substrate.

5'-CAAGCAGAAGACGGCATACGAGAT<barcode>GTGACTGGAGTTCAGACGTGTGCT CTTCCGATC-TACTCGAG-3'—A 3' sequence includes a sequence that is identical to the 5' fixed nucleotide sequence (5'-GCTCTTCCGATCTACTCGAG-3' (SEQ ID NO: 18)) of the amplifying primer, and a P5 read sequence that is identical or complimentary to a P5 read sequence primer, a specific identifier sequence of choice ("barcode") and a P7 adapter sequence (5'-CAAGCAGAAGACGGCAT-ACGAGAT-3' (SEQ ID NO: 21)) that is identical or complimentary to a P7 nucleotide sequence attached to a solid substrate. The entire primer sequence is 5'-CAAGCAGAA-GACGGCATACGAGATXXXXXXXXGTGACTG-GAGTTCAGACGTGT GCTCTTCCGATCTACTCGAG-3' (SEQ ID NO: 22), wherein XXXXXXXX is a specific sequence of choice.

Figure 23:
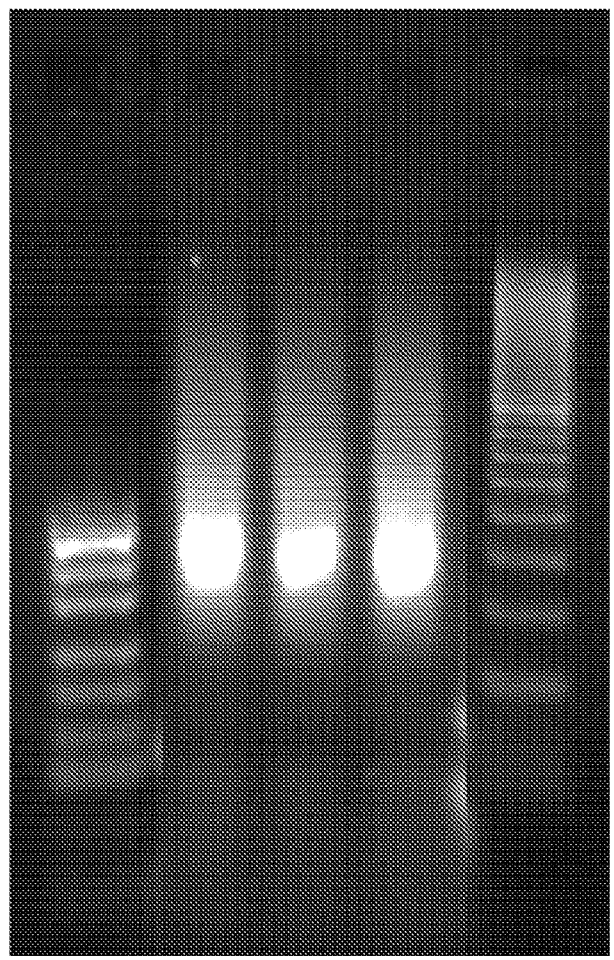
FIG. 23 shows PCR product after electrophoresis for an embodiment of the PCR barcoding method according to a further embodiment of the present disclosure.

FIG. 23 shows PCR product after electrophoresis through a 1% agarose gel for an embodiment of the PCR barcoding method.

EXAMPLE 7

PCR Barcoding Using Barcoded Amplifying Primer v3

A schematic representation of another work flow according to a further embodiment is provided in FIG. 24.

Protocols for use in this workflow are described in the previous examples.

Step 1—WGA and Barcoding PCR

5'-GCTCTTCCGATCT<barcode>GAGNNNNNNATG-TGG-3'—Amplifying primer with a degenerate nucleotide sequence (5'-NNNNNN-3'), a barcode sequence, and a 5' fixed sequence (5'-GCTCTTCCGATCT-3' (SEQ ID NO: 26)).

Step 2—Adapter PCR

5'-AATGATACGGCGACCACCGAGATCTA-CACTCTTTCCCTACACGACGCTCTTCCGA TCT-3' (SEQ ID NO: 50)—A 3' sequence that includes sequence that is identical to the 5' fixed nucleotide sequence (5'-

GCTCTTCCGATCT-3' (SEQ ID NO: 18)) of the amplifying primer, and a P5 read sequence that is identical or complementary to a P5 read sequence primer and a P5 adapter sequence (5'-AATGATACGGCGACCACCGAGATCT-3' (SEQ ID NO: 49)) that is identical or complementary to a P5 nucleotide sequence attached to a solid substrate.

5'-CAAGCAGAAGACGGCATACGAGATGTGACTG-GAGTTCAGACGTGTGCTCTTCCG ATCT-3' (SEQ ID NO: 51)—A 3' sequence that includes sequence that is identical to the 5' fixed nucleotide sequence (5'-GCTCTTCCGATCT-3' (SEQ ID NO: 18)) of the amplifying primer, and a P5 read sequence that is identical or complementary to a P5 read sequence primer and a P7 adapter sequence (5'-CAAGCAGAAGACGGCATACGAGAT-3' (SEQ ID NO: 21)) that is identical or complementary to a P7 nucleotide sequence attached to a solid substrate.

Figure 25:
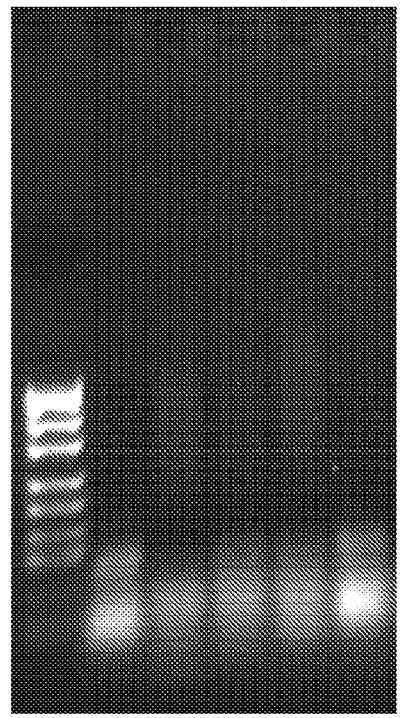
FIG. 25 shows PCR product after electrophoresis for an embodiment of the PCR barcoding method according to a further embodiment of the present disclosure.
Figure 26:
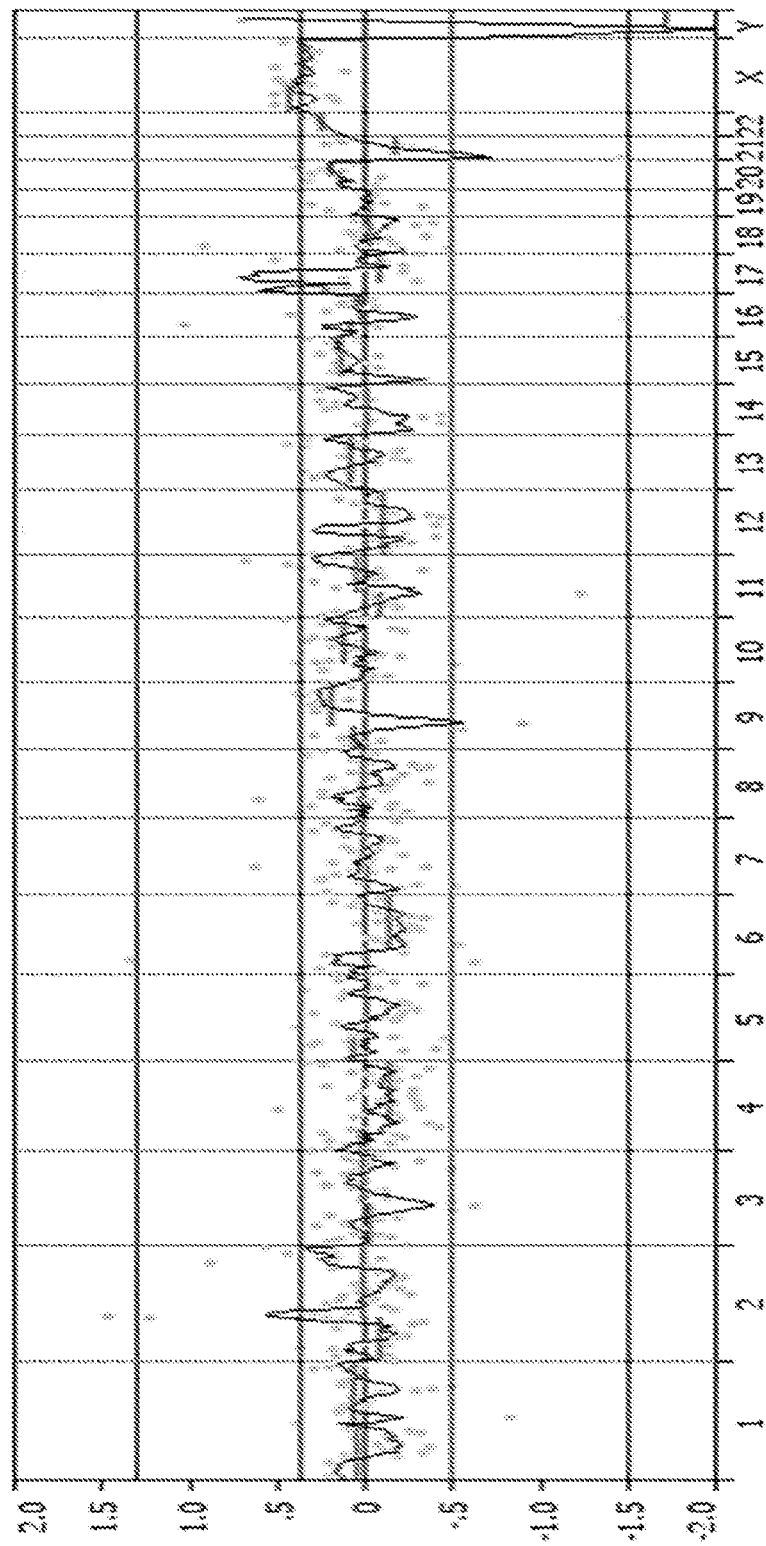
FIG. 26 shows a 5-cell sample result with a euploid female (G00318; PerkinElmer Health Sciences (Australia) Pty Ltd (PKHS(A) Pty Ltd), according to a further embodiment of the present disclosure.

FIG. 25 shows PCR product after electrophoresis through a 1% agarose gel for an embodiment of the PCR barcoding method. FIG. 26 shows a 5-cell sample result with a euploid female (G00318; PKHS(A) Pty Ltd), according to a second embodiment of the present disclosure.

Conclusions

This embodiment provides a single tube amplification and barcoding protocol for sequencing on Illumina (US) NGS platforms to allow rapid, scalable and economical sequencing for PGT-A from a single embryo biopsy. The benefit of this protocol is the ability to barcode during the first round, allowing streamlining of downstream processes.

Although the present disclosure has been described with reference to particular embodiments, it will be appreciated that the disclosure may be embodied in many other forms. It will also be appreciated that the disclosure described herein is susceptible to variations and modifications other than those specifically described. It is to be understood that the disclosure includes all such variations and modifications. The disclosure also includes all of the steps, features, compositions and compounds referred to, or indicated in this specification, individually or collectively, and any and all combinations of any two or more of the steps or features.

Also, it is to be noted that, as used herein, the singular forms "a", "an" and "the" include plural aspects unless the context already dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Reference to any prior art in this specification is not, and should not be taken as, an acknowledgment or any form of suggestion that this prior art forms part of the common general knowledge in any country.

The subject headings used herein are included only for the ease of reference of the reader and should not be used to limit the subject matter found throughout the disclosure or the claims. The subject headings should not be used in construing the scope of the claims or the claim limitations.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

Future patent applications may be filed on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the present disclosure. Features may be added to or omitted from the example claims at a later date.

The invention claimed is:

1. A method of producing nucleic acid for sequencing utilising clonal amplification on a solid substrate, the method comprising:
   (a) providing a nucleic acid sample for sequencing;
   (b) amplifying the nucleic acid sample using:
      an amplifying primer comprising a degenerate nucleotide sequence and a 5' fixed nucleotide sequence; and
      one or more target specific primers,
   to produce amplified nucleic acids; and
   (c) further amplifying the amplified nucleic acids with (i) a first primer comprising the 5' fixed nucleotide sequence and a first adapter nucleotide sequence, and (ii) a second primer comprising the 5' fixed nucleotide sequence and a second adapter nucleotide sequence, wherein the first adapter nucleotide sequence or the second adapter nucleotide sequence provides a sequence for subsequent priming of DNA synthesis from a nucleotide sequence attached to the solid substrate and the other adapter nucleotide sequence provides a sequence for subsequent priming of DNA synthesis from a template produced from the subsequent priming, and wherein one or more of the first primer, the second primer and the amplifying primer comprise a specific identifier sequence to identify nucleic acids amplified with the first primer, the second primer and/or the amplifying primer;
   thereby producing nucleic acid for sequencing utilising clonal amplification on the solid substrate.

2. The method according to claim 1, wherein the amplifying primer comprises a degenerate nucleotide sequence consisting of 6 nucleotides.

3. The method according to claim 1, wherein the amplifying primer comprises a fixed nucleotide sequence 3' to the degenerate nucleotide sequence.

4. The method according to claim 3, wherein the fixed nucleotide sequence 3' to the degenerate nucleotide sequence consists of a nucleotide sequence of 6 nucleotides.

5. The method according to claim 3, wherein the fixed nucleotide sequence 3' to the degenerate nucleotide sequence consists of the nucleotide sequence 5'-ATGTGG-, 5'-ATCTCA-3' or TGAGAT.

6. The method according to claim 1, wherein the 5' fixed nucleotide sequence consists of a nucleotide sequence of 10 nucleotides.

7. The method according to claim 1, wherein the 5' fixed nucleotide sequence consists of the nucleotide sequence 5'-CCAGCCTTGC-3' (SEQ ID NO: 2), 5'-CCGACTCGAG-3' (SEQ ID NO: 23), 5'-GATGCTCGAG-3' (SEQ ID NO: 24), 5'-GATGCCTTGC-3' (SEQ ID NO: 25), 5'-GCTCTTCCGATCT-3' (SEQ ID NO: 26), 5'-GCTCTTCCGATCTACTCGAG-3' (SEQ ID NO: 27), 5'-GCTCTTCCGATCTGAG-3' (SEQ ID NO: 18), 5'-AGTTCAGACGTGTGCTCTTCCGATCT-3' (SEQ ID NO: 28) or 5'-CAGACGTGTGCTCTTCCGATCT-3' (SEQ ID NO: 29).

8. The method according to claim 1, wherein the first adapter nucleotide sequence comprises the nucleotide sequence 5'-CCGCTTTCCTCTCTATGGGCAGTCGGTGAT-3' (SEQ ID NO: 11) or 5'-CCTCTCTATGGGCAGTCGGTGAT-3' (SEQ ID NO: 47).

9. The method according to claim 1, wherein the second adapter nucleotide sequence comprises the nucleotide sequence 5'-CCATCTCATCCCTGCGTGTCTCCGACTCAG-3' (SEQ ID NO: 14).

10. The method according to claim 1, wherein the first primer comprises a first adapter nucleotide sequence for subsequent priming of DNA synthesis and the second primer comprises a second adapter sequence which is identical or complementary to a nucleotide sequence attached to the solid substrate.

11. The method according to claim 1, wherein the first primer and the second primer comprise a nucleotide sequence which is identical or complementary to a nucleotide sequence attached to the solid substrate.

12. The method according to claim 1, wherein the specific identifier sequence consists of a nucleotide sequence of 10 nucleotides.

13. The method according to claim 1, wherein the specific identifier sequence comprises the nucleotide sequence 5'-TCTAACGGAC-3 (SEQ ID NO: 3).

14. The method according to claim 1, wherein the amplifying primer comprises a specific identifier sequence, the first primer comprises a first adapter sequence for subsequent priming of DNA synthesis, and the second primer comprises a nucleotide sequence identical or complementary to a nucleotide sequence attached to the solid substrate and a specific identifier sequence.

15. The method according to claim 1, wherein the first primer comprises a first adapter sequence for subsequent priming of DNA synthesis and a specific identifier sequence, and the second primer comprises a nucleotide sequence identical or complementary to a nucleotide sequence attached to the solid substrate.

16. The method according to claim 1, wherein the first primer comprises a first adapter sequence for subsequent priming of DNA synthesis and a nucleotide sequence identical or complementary to a nucleotide sequence attached to the solid substrate, and the second primer comprises a nucleotide sequence identical or complementary to another nucleotide sequence attached to the solid substrate and a specific identifier sequence.

17. The method according to claim 1, wherein the method further comprises further amplifying with the one or more target specific primers in step (c).

* * * * *